US012599454B2

(12) United States Patent
Holland et al.

(10) Patent No.: US 12,599,454 B2
(45) Date of Patent: Apr. 14, 2026

(54) MECHANISMS AND METHODS TO CONTROL MOVEMENT OF A HEAD OF A MEDICAL SYSTEM RELATIVE TO AN ANATOMICAL SITE

(71) Applicant: ViaLase, Inc., Aliso Viejo, CA (US)

(72) Inventors: Guy Holland, San Juan Capistrano, CA (US); Virginia Lin, Newport Beach, CA (US); Wesley W. Lummis, Rancho Santa Margarita, CA (US); Ferenc Raksi, Mission Viejo, CA (US); Nathan Sangalang, Aliso Viejo, CA (US); Joselito T. Tambo, Irvine, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 576 days.

(21) Appl. No.: 17/993,581

(22) Filed: Nov. 23, 2022

(65) Prior Publication Data

US 2024/0164862 A1    May 23, 2024

(51) Int. Cl.
A61B 90/00        (2016.01)
A61F 9/009        (2006.01)
            (Continued)

(52) U.S. Cl.
CPC .............. A61B 90/03 (2016.02); A61F 9/009 (2013.01); A61B 2090/034 (2016.02);
            (Continued)

(58) Field of Classification Search
CPC .............. A61B 90/03; A61B 2090/034; A61B 2090/064; A61B 2090/5025;
            (Continued)

(56) References Cited

U.S. PATENT DOCUMENTS

| 5,316,260 A | 5/1994 | Johnston |
|---|---|---|
| 5,336,215 A | 8/1994 | Hsueh et al. |

(Continued)

FOREIGN PATENT DOCUMENTS

| CN | 204988055 U | 1/2016 |
|---|---|---|
| CN | 107951564 A1 | 4/2018 |

(Continued)

OTHER PUBLICATIONS

International Search Report and Written Opinion, PCT/US2023/079773, May 6, 2024, 20 pgs.

(Continued)

*Primary Examiner* — Aaron F Roane

(74) *Attorney, Agent, or Firm* — LOZA & LOZA, LLP; David S. Sarisky

(57) ABSTRACT

A delivery arm assembly of a medical system includes a head having an end arranged to face a reference plane and a multistage slide mechanism coupled to the head. The multistage slide mechanism includes a long-range slide mechanism configured to move the head in a direction toward the reference plane and a short-range slide mechanism coupled with the long-range slide mechanism. The short-range slide mechanism is configured to stop further movement of the head in the direction toward the reference plane in response to a resistive force against movement of the head toward the reference plane.

20 Claims, 21 Drawing Sheets

(51) Int. Cl.
    *A61B 90/50*       (2016.01)
    *A61F 9/008*      (2006.01)

(52) U.S. Cl.
    CPC . *A61B 2090/064* (2016.02); *A61B 2090/5025*
        (2016.02); *A61B 2090/508* (2016.02); *A61F*
           *2009/00851* (2013.01); *A61F 2009/00897*
                         (2013.01)

(58) Field of Classification Search
    CPC .............. A61B 2090/508; A61F 9/009; A61F
                        2009/00851; A61F 2009/00897
    USPC .......................................................... 606/4
    See application file for complete search history.

(56) References Cited

U.S. PATENT DOCUMENTS

| | | |
|---|---|---|
| 5,642,392 A | 6/1997 | Nakano et al. |
| 5,644,375 A | 7/1997 | Suzuki |
| 5,695,500 A | 12/1997 | Taylor et al. |
| 6,082,506 A | 7/2000 | Huang et al. |
| 7,428,855 B2 | 9/2008 | Duval |
| 7,554,723 B2 | 6/2009 | Moeller et al. |
| 7,677,540 B1 | 3/2010 | Duval |
| 7,798,035 B2 | 9/2010 | Duval |
| 8,771,262 B2 | 7/2014 | Rathjen |
| 8,858,539 B2 | 10/2014 | Rathjen |
| 8,939,965 B2 | 1/2015 | Liesfeld et al. |
| 9,060,848 B2 | 6/2015 | Rathjen |
| 9,301,807 B2 | 4/2016 | Duval |
| 2009/0118717 A1 | 5/2009 | Brownell |
| 2010/0168762 A1* | 7/2010 | Osawa .................... A61F 9/007 |
| | | 74/490.11 |
| 2014/0005831 A1 | 1/2014 | Naderer et al. |
| 2021/0038426 A1 | 2/2021 | Boularot et al. |

FOREIGN PATENT DOCUMENTS

| | | |
|---|---|---|
| CN | 113017839 A | 6/2021 |
| CN | 113021412 A | 6/2021 |
| EP | 3479775 A1 | 5/2019 |
| JP | H0647003 A | 2/1994 |
| WO | 2009072535 A1 | 6/2009 |

OTHER PUBLICATIONS

Shin et al.; "Variable Radius Pulley Design Methodology for Pneumatic Artificial Muscle-based Antagonistic Actuation Systems"; 2011 IEEE/RSJ International Conference on Intelligent Robots and Systems; Sep. 25-30, 2011; San Francisco, California, USA; pp. 1830-1835.

Tadakuma et al.; "Floating Displacement—Force Conversion Mechanism as a Robotic Mechanism"; Jul. 22, 2019; https://arxiv.org/abs/1907.09955; 6 pages.

Kerr; "Magnetic Counterbalances for High Performance Vertical Stages"; Mar. 11, 2022; 4 pages.

International Preliminary Report on Patentability (Oct. 29, 2024).

* cited by examiner

SECOND-STAGE VERTICAL DISPLACEMENT
(FINE FLOAT RANGE)

554 → UPPER LIMIT, HARD STOP

560 → UPPER FORCE LIMIT. ACTIVATION OF COARSE FLOAT BRAKE

558 → ACTIVATION OF CONE LOCK

556 → LOWER LIMIT, HARD STOP (CONE CONTACT)

10mm-60mm

FIRST-STAGE VERTICAL DISPLACEMENT
(COARSE FLOAT RANGE)

550 → UPPER LIMIT, HARD STOP

552 → LOWER LIMIT, HARD STOP

75mm-125mm

SECURE PATIENT
INTERFACE TO EYE — 602

ENABLE MOVEMENT OF
SURGICAL HEAD — 604

ENABLE A FINE-FLOAT MOVEMENT OF SURGICAL
HEAD AWAY FROM PATIENT INTERFACE — 606

LOCK SURGICAL HEAD TO
PATIENT INTERFACE — 608

RESTRICT MOVEMENT OF
THE SURGICAL HEAD — 610

REDUCE WEIGHT — 612

RELEASE SURGICAL HEAD FROM PATIENT
INTERFACE AND PATIENT INTERFACE FROM EYE — 614

ENABLE MOVEMENT OF
THE SURGICAL HEAD — 616

| | MOVES TOWARD ANATOMICAL SITE 1 |
| --- | --- |
| | DOES NOT MOVE TOWARD ANATOMICAL SITE 1 |

MECHANISMS AND METHODS TO CONTROL MOVEMENT OF A HEAD OF A MEDICAL SYSTEM RELATIVE TO AN ANATOMICAL SITE

TECHNICAL FIELD

The present disclosure relates generally to the field of medical systems having a system head, and more particularly to mechanisms and methods for enabling and controlling movement of the system head relative to an anatomical site.

BACKGROUND

As part of a medical procedure, a head of a medical system may be manually placed relative to an anatomical site for purposes of conducting a diagnostic procedure, an imaging procedure, a surgical procedure, or a combination of two or more of these procedures. For example, in ophthalmic surgery a patient may be supine on a surgical bed with his eye facing a surgical head of an ophthalmic surgical system and a surgeon may maneuver the surgical head laterally and up and down relative to the eye in order to couple the surgical head to the eye. In some cases, a patient interface is connected and secured to the eye and a cone attachment of a surgical head is connected to the patient interface. The patient interface is positioned between the eye and the surgical head to immobilize the eye relative to the ophthalmic surgical system.

Maneuvering of the surgical head relative to the eye, especially downward movement of the head toward the eye, may result in contact between the head and the eye that produces an unacceptable force on the eye that can lead to injury. It is therefore desirable to have surgical systems with mechanisms that protect against these unacceptable forces.

SUMMARY

The present disclosure relates to a method of moving a head of a medical system relative to an anatomical site. The method includes moving the head in a direction toward the anatomical site, and in response to a resistive force against movement of the head in the direction toward the anatomical site, stopping further movement of the head in the direction toward the anatomical site. Movement of the head in the direction toward the anatomical site is enabled by a long-range slide mechanism that is coupled to the head, while stoppage of further movement of the head in that direction is enabled by a short-range slide mechanism that is coupled between the long-range slide mechanism and the head.

The present disclosure also relates to a delivery arm assembly of a medical system. The delivery arm assembly includes a head having an end arranged to face a reference plane and a multistage slide mechanism coupled to the head. The multistage slide mechanism includes a long-range slide mechanism configured to move the head in a direction toward the reference plane and a short-range slide mechanism coupled with the long-range slide mechanism. The short-range slide mechanism is configured to stop further movement of the head in the direction toward the reference plane in response to a resistive force against movement of the head toward the reference plane.

The present disclosure also relates to a medical system having a delivery arm assembly and a brake system. The delivery arm assembly includes a head having an end arranged to face a reference plane, a delivery arm configured to enable lateral movement of the head relative to the reference plane, and a multistage slide mechanism. The multistage slide mechanism includes a long-range slide mechanism configured to enable movement of the head in a direction toward the reference plane, and a short-range slide mechanism coupled with the long-range slide mechanism and configured to, in response to a resistive force against movement of the head toward the reference plane, stop further movement of the head in the direction toward the reference plane. The brake system is configured to transition between a locked state and an unlocked state. In the locked state, lateral movement of the head through the delivery arm is prevented and movement of the head through the long-range slide mechanism is prevented. In the unlocked state, lateral movement of the head through the delivery arm is enabled and movement of the head through the long-range slide mechanism is enabled.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, apparatuses, and methods will now be presented in the detailed description by way of example, and not by way of limitation, with reference to the accompanying drawings, wherein.

DETAILED DESCRIPTION

Disclosed herein are medical systems having mechanisms that enable and control movement of a head relative to an anatomical site. The medical system may be a diagnostic system configured to conduct a diagnostic procedure at a diagnostic site, an imaging system configured to image an imaging site, a surgical system configured to conduct a surgical procedure at a surgical site, or a combination of two or more of these systems. The systems include a delivery arm assembly comprising a head and a multistage slide mechanism coupled to the head. The multistage slide mechanism includes a long-range slide mechanism (or coarse-float mechanism) and a short-range slide mechanism (or fine-float mechanism). The long-range slide mechanism is configured to move the head in a direction toward a reference plane. The reference plane may, for example, correspond to bed upon which a patient with an anatomical site may lie during a procedure. The procedure may be a diagnostic procedure, an imaging procedure, a surgical procedure, or a combination of two or more of these procedures.

To protect against unnecessary forces on an anatomical site, the short-range slide mechanism is configured to automatically stop movement of the head in a direction toward the reference plane, in response to a resistive force (our counter force) against continued movement of the head toward the reference plane by the long-range slide mechanism.

To protect against prolonged applications of an initial force to an anatomical site, the short-range slide mechanism is further configured to limit a force applied to a site through the head to an initial force, and to automatically reduce the force applied to the site through the head to a reduced force less than the initial force in response to a presence of a triggering event. The triggering event may be, for example, an attachment between the head and a patient interface that is coupled to the anatomical site, e.g., eye, of a patient.

To further protect against unnecessary forces on an anatomical site, the long-range slide mechanism is configured to, in response to a presence of a first triggering event, prevent movement of the head toward the reference plane while simultaneously allowing movement of the head away from the reference plane. The triggering event may be, for example, an attachment between the head and a patient interface that is coupled to the anatomical site, e.g., eye, of a patient.

The medical system disclosed in detail going forward in this specification includes components and apparatuses that provide imaging, diagnostics, and surgical capability. Accordingly, while the medical system is referred to as an ophthalmic surgical system, it may also be considered an imaging system and/or a diagnostic system.

Ophthalmic Surgical System

Figure 1:
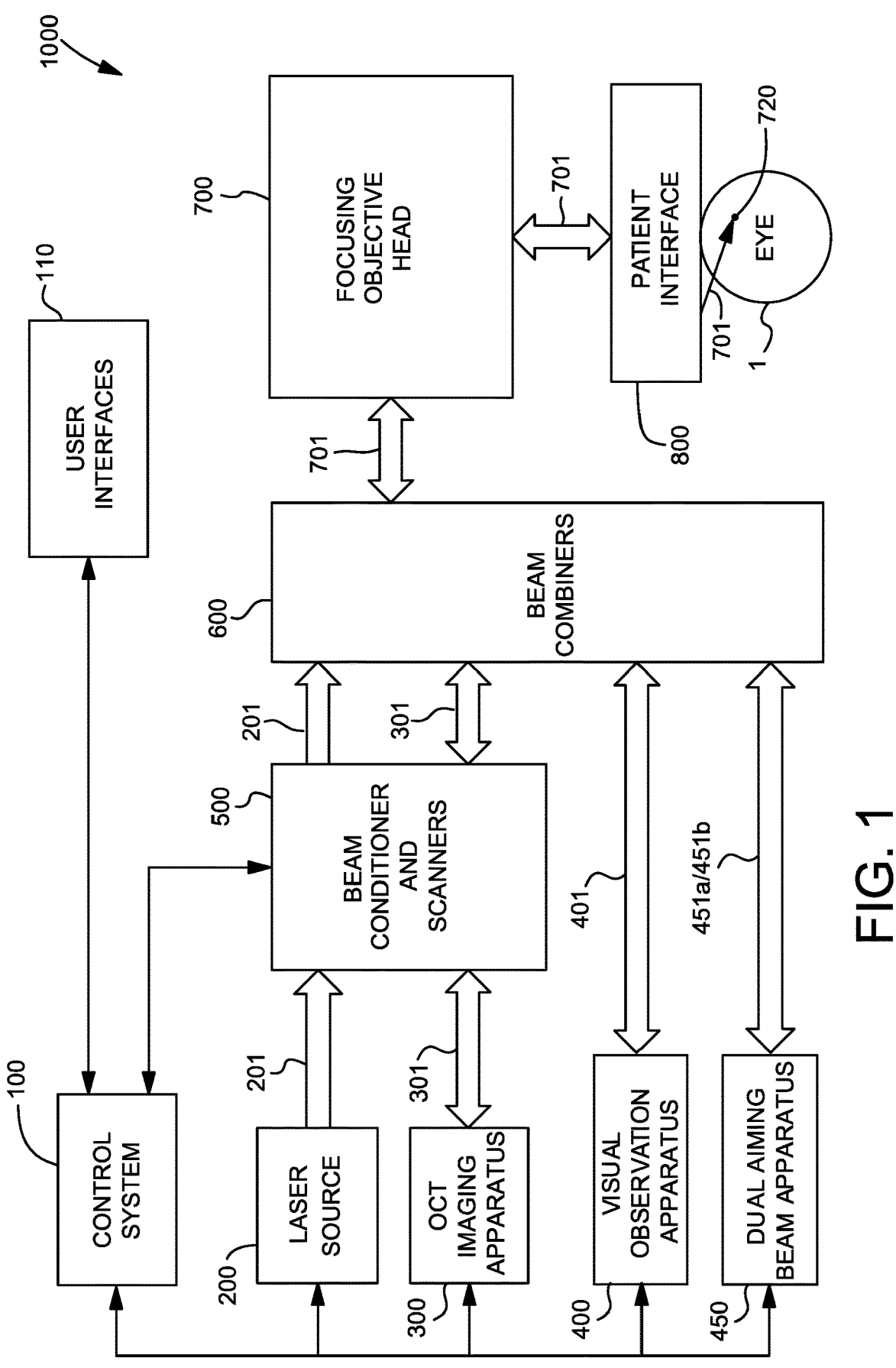
FIG. 1 is a block diagram of an ophthalmic surgical system having a focusing objective head, also referred to as a surgical head, that couples to an eye through a patient interface.

With reference to FIG. 1, an ophthalmic surgical system 1000 for non-invasive surgery includes a control system 100, one or more user interfaces 110, a surgical component 200, one or more imaging/visual components 300, 400, and a target locating apparatus 450. Other components of the integrated surgical system 1000 include beam conditioners and scanners 500, beam combiners 600, and a focusing objective head 700 that couples with a patient interface 800.

The surgical component 200 may be a femtosecond laser source that outputs a laser beam 201. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high.

A first imaging/visual component 300 may be an OCT imaging apparatus that outputs an OCT beam 301. OCT technology provides imagery that assist in diagnosing, locating, and guiding laser surgery directed to different tissue targets in the eye. For example, OCT imaging may be used to determine the structural and geometrical conditions of the irido-corneal angle and to determine the accessibility of the ocular tissue for treatment. OCT imaging can provide the necessary spatial resolution, tissue penetration and contrast to resolve microscopic details of ocular tissue.

A second imaging/visual component 400 may a visual observation apparatus that outputs a visual observation beam 401 and an illumination source. The visual observation apparatus 400 provides imagery that assist in identifying surgical locations. The visual observation apparatus may include, for example, a video camera and a telescope. The camera may be a digital camera fitted with a goniolens to provide gonioscopic images of the eye. The illumination source is positioned for optimal irradiance of the object of interested, e.g., tissue targets in the eye. Illumination sources may be LEDs or light delivered via fiber optic cables.

The target locating apparatus 450 may be a dual aiming beam apparatus such as disclosed in U.S. Patent Application Publication No. 2021/0235986, title "System and Method for Locating a surface of Ocular Tissue for Glaucoma Surgery Based on Dual Aiming Beams," the contents of which are incorporated herein by reference. The dual aiming beam apparatus 450 outputs a pair of beams of light, referred to herein as dual aiming beams 451a/451b, for use in detecting a surface of ocular tissue in a surgical field.

The beam conditioner and scanners 500 are configured to set beam parameters of light beams including beam size and divergence. Beam conditioning may also include additional functions, such as setting the beam power or pulse energy and shutter the beam to turn it on or off. As shown in FIG. 1, a laser beam 201 from the femtosecond laser source 200 and an OCT beam 301 from the OCT imaging apparatus 300 are directed towards the beam conditioners and scanners 500. The beam conditioners and scanners 500 include components, e.g., scanning mirrors, for scanning the laser beams 201 and OCT beams 301 independent of each other. Different kind of scanners can be used for the purpose of scanning the laser beam 201 and the OCT beam 301. For scanning transversal to a light beam 201, 301, angular scanning galvanometer scanners are available for example from Cambridge Technology, Bedford, MA, Scanlab, Munich, Germany.

The beam combiners 600 are configured to split and combine light beams. The beam combiners 500 may include dichroic or polarization beam splitters that split and recombine light beams with different wavelength and/or polarization. The beam combiner 600 may also include optics to change certain parameters of the individual light beams such as beam size, beam angle and divergence. As shown in FIG. 1, two or more of the laser beam 201, the OCT beam 301, the visual observation beam 401, and the dual aiming beams 451*a*/451*b* may be combined with dichroic, polarization or other kind of beam combiners 600 and provided to the focusing objective head 700 as a combined light beam 701 to reach a common target volume 720 of ocular tissue of the eye 1.

The focusing objective head 700 is optically coupled to receive a combined light beam 701 from the beam combiner 600 and to direct the received combined light beam into alignment with a common target volume 720 of ocular tissue of the eye 1.

The control system 100 is connected to the other components 200, 300, 400, 450, 500, 700 of the integrated surgical system 1000. The control system 100 may be a single computer or and plurality of interconnected computers configured to control the hardware and software components of the other components of the ophthalmic surgical system 1000. A user interface 110 of the control system 100 may present a graphical user interface (GUI) that accepts instructions from a user and displays information for observation by the user. Input information and commands from the user include but are not limited to system commands, motion controls for docking the patient's eye to the system, selection of pre-programmed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam parameters, and the acquiring, analyzing, and displaying of OCT images of tissue in the surgical field.

Control signals from the control system 100 to the dual aiming beam apparatus 450 function to control the output of beams of light by the one or more aiming beam sources of the dual aiming beam apparatus. Control signals from the control system 100 to the visual observation apparatus 400 function to control the capturing, image processing and displaying of video images of tissue in the surgical field and spots of light on tissue surfaces in the surgical field that result from the one or more beams of light output by the dual aiming beam apparatus 450. To this end, the line of sight of the visual observation apparatus 400 may be aligned with the femtosecond laser and directed into the target area of the eye.

Control signals from the control system 100 to the beam conditioner and scanners 500 function to control the scanning of a laser beam output by the femtosecond laser source 200 and the scanning of an OCT beam output by the OCT imaging apparatus 300. Control signals to the beam conditioner and scanners 500 may include location, size and shape of surgical patterns expressed in position coordinates of the intended location of focus of the laser and the scanning path of the laser across the surgical volume. These types of control signals can be pre-programmed, with one or more control parameters selectable by the operator. The control parameters of the surgical pattern may include the location of the pattern, the shape, length, width and depth of the pattern, laser spot, line and layer separation and energy of the laser pulses. Control signals to and from various subsystems and components are calibrated prior to operating the surgical system. The calibration includes calibrating the pixel coordinates acquired and displayed by the visual observation apparatus 400 and the OCT imaging apparatus 300 to actual physical coordinates in the eye and includes calibrating commanded motions of the OCT and laser scanner systems to actual OCT and laser beam displacements in the eye.

Control signals from the control system 100 to the focusing objective head 700 may function to control axial scanning of either or both of a laser beam 201 and an OCT beam 301 through a motorized focusing objective.

Commanding the integrated surgical system 1000 to make a surgical incision includes docking the system on the eye, acquiring, and displaying visual observation images including spots from the dual aiming beams, and OCT images on a computer screen, determining the coordinate location and other parameters of the intended surgical incision based on the displayed images and instructing the control system 100 to execute the surgical pattern based on information collected from those images. The parameters based on the images may be determined by the operator of the integrated surgical system 1000 or may be determined by an image processing and analyzing computer algorithm. Instructions using these parameters can be given by the operator as entering input data in the form of text, mouse clicks and drag and drop commands on the computer screen. Alternatively, a system processor that may be included in the control system 100 generates instructions for execution by the control system based on the previously determined parameters.

Figure 2:
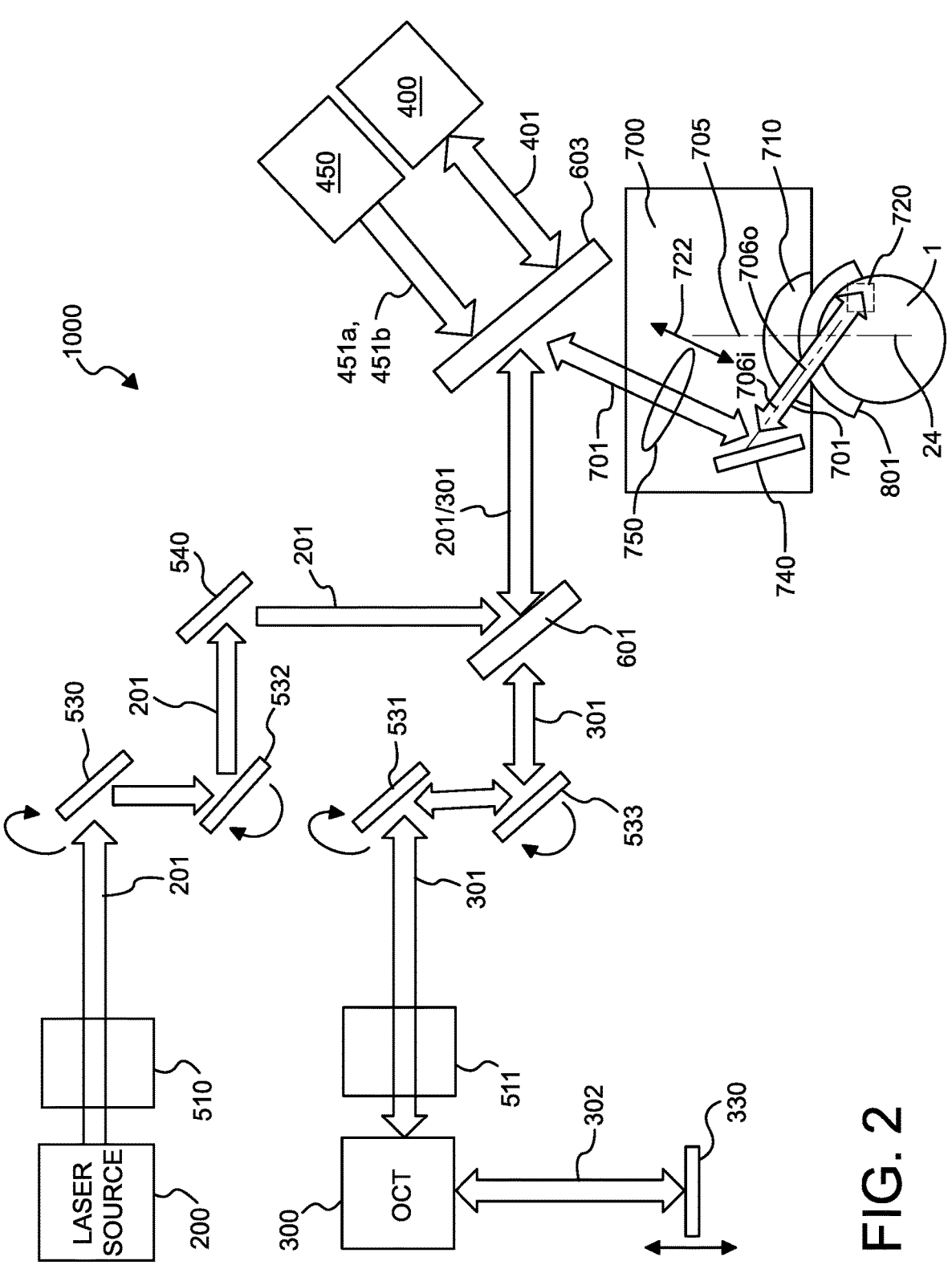
FIG. 2 is a detailed block diagram of an embodiment of the ophthalmic surgical system of FIG. 1.

Referring to FIG. 2, an integrated surgical system may be configured to deliver one or more of a laser beam 201, an OCT beam 301, a visual observation beam 401, and a pair of aiming beams of light 451*a*, 451*b* in the distal direction toward an eye 1 along a beam path, and to receive one or more of an OCT return beam 301 and a visual observation reflection beam 401 back from the eye 1 along the single beam path. In the example embodiment of FIG. 2, the single beam path is into a target volume 720 of ocular tissue of the eye in the irido-corneal angle.

Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, a pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511 and a transversal scanner with scanning mirrors 531 and 533.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 210/301 are multiplexed and travel in the same direction. The combined laser/OCT beam 210/301 propagates to a second beam combining mirror 603 where it is combined with one or more aiming beams of light 451a/451b and a visual observation beam 401 to form a combined laser/OCT/visual/aiming beam 701a.

The combined light beam 701 traveling in the distal direction passes through a focusing objective 750 and is reflected by an alignment mechanism 740, e.g., a beam-folding mirror, into alignment with an input axis 706i of an exit lens 710. The combined light beam 701 passes through the exit lens 710 and exits the exit lens along an output axis 706o and into and through a window 801 of a patient interface into a focal point in the target volume 720. The focusing objective 750, which may include a single lens or a group of lenses, is movable in the axial direction 722 by a servo motor, stepper motor or other control mechanism. Movement of the focusing objective 750 in the axial direction 722 changes the axial distance of the focus of the laser beam 201 and the OCT beam 301 at a focal point.

A scattered OCT return beam 301 from the target volume 720 of ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300.

Figure 3A:
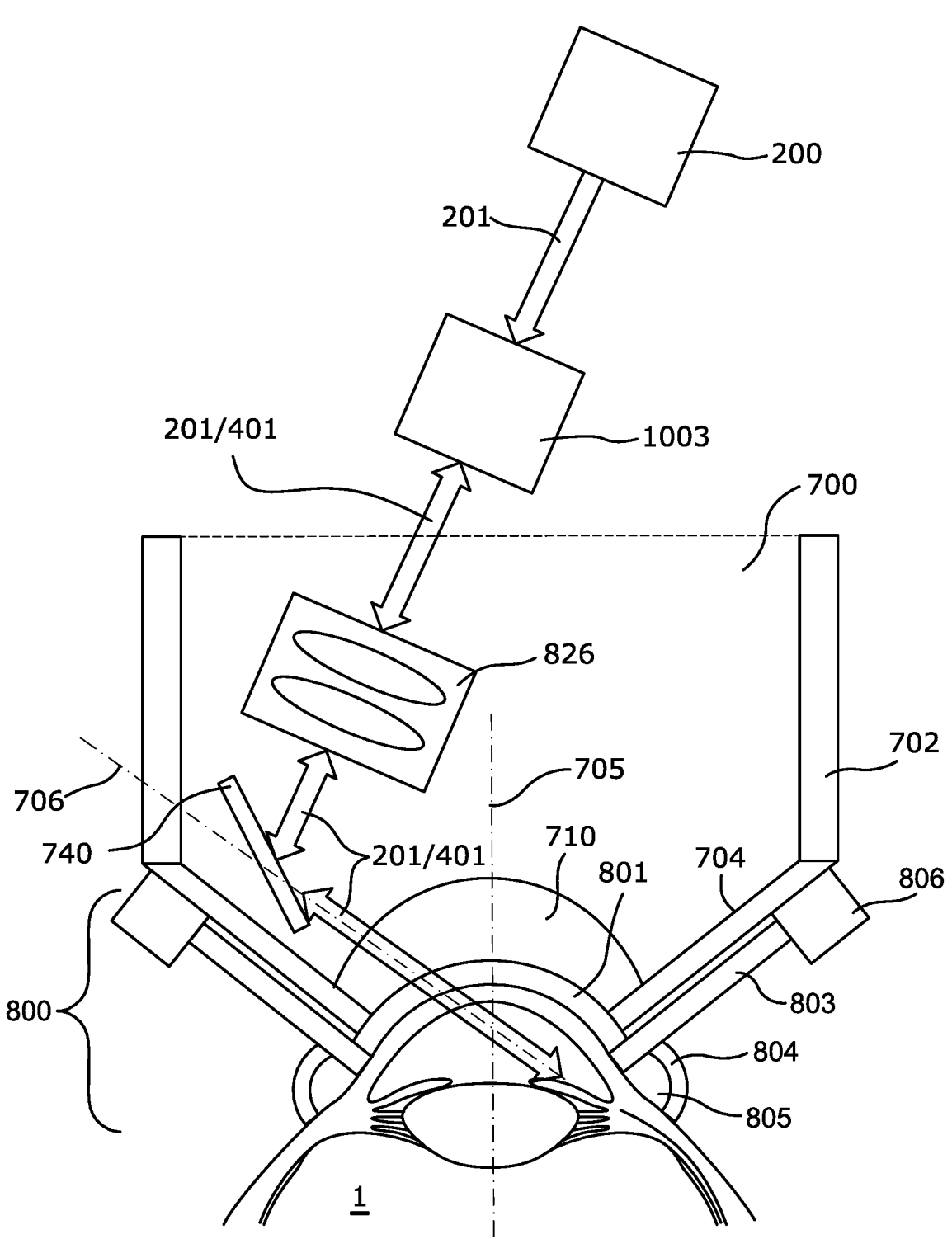
FIGS. 3A and 3B are schematic illustrations of a surgical head of an ophthalmic surgical system coupled to (FIG. 3A) and decoupled from (FIG. 3B) a patient interface.
Figure 3B:
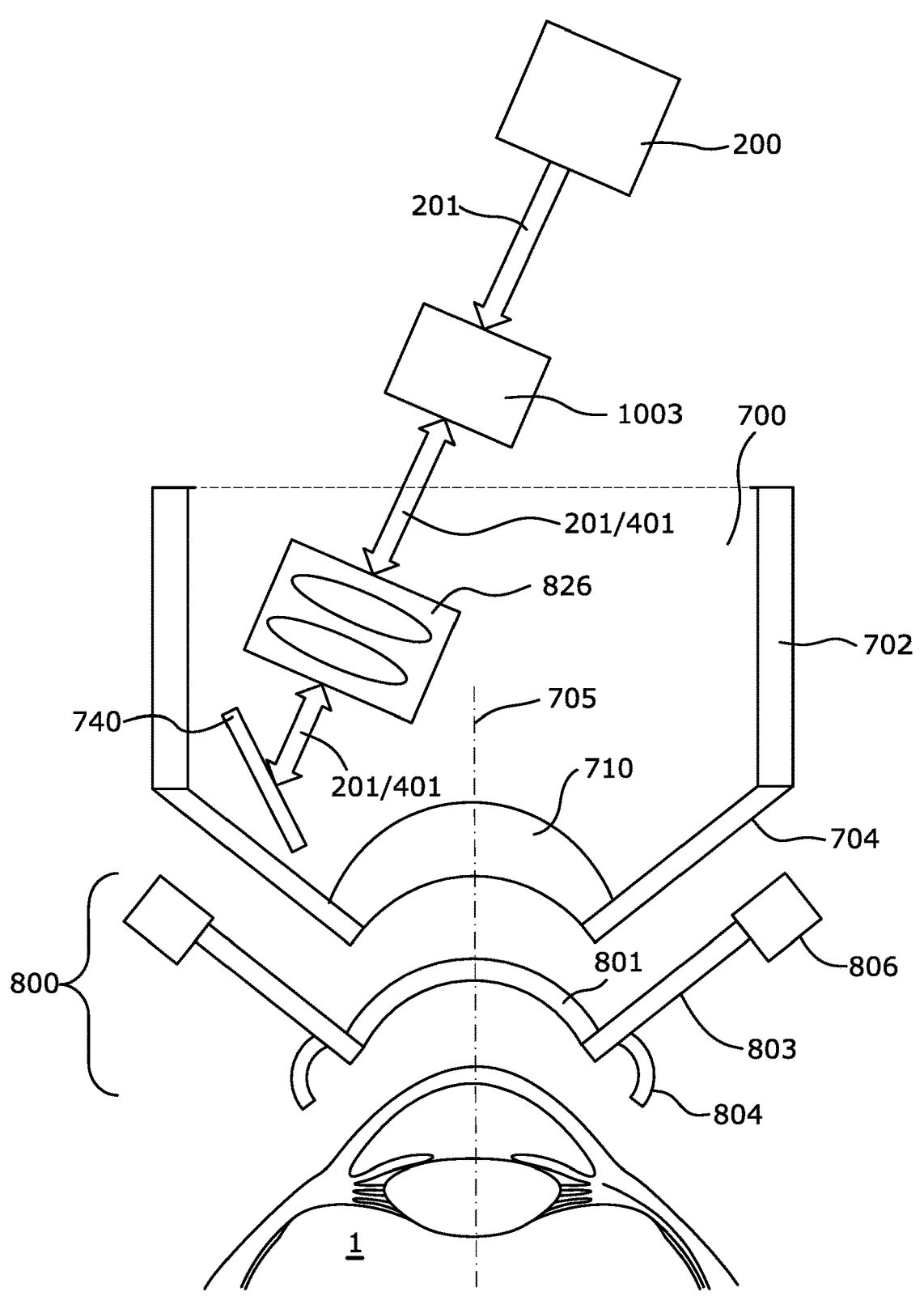

With reference to FIGS. 3A and 3B, the focusing objective head 700 optically and physically couples to the eye 1 through a patient interface 800. The focusing objective head 700 includes a housing 702 that houses components of the ophthalmic surgical system 1000, including for example, the exit lens 710, the alignment mechanism 740, and the focusing objective 826. The housing 702 includes a cone attachment 704 that surrounds the exit lens 710. As described below, the cone attachment 704 is configured to couple with the patient interface 800 in a manner that secures or locks the cone attachment to the patient interface.

Regarding the exit lens 710, in one configuration, the exit lens is an aspheric lens having an eye-facing, concave surface 711 and a convex surface 712 opposite the concave surface. The exit lens 710 thus has a meniscus form. While the exit lens 710 shown in FIGS. 3A and 3B is an aspheric lens giving more design freedom, in other configurations the exit lens may be a spherical lens. Alternatively, the exit lens 710 may be a compound lens, as opposed to a singlet.

Continuing with reference to FIGS. 3A and 3B, the patient interface 800 physically couples to the eye 1 on one side and to the focusing objective head 700 on another side. The patient interface 800 serves multiple functions. It immobilizes the eye 1 relative to components of the ophthalmic surgical system 1000; creates a sterile barrier between the components and the patient; and provides optical access between the eye and components of the ophthalmic the surgical system. The patient interface 800 may be a sterile, single use disposable device.

In some configurations, the patient interface 800 includes the window 801. The window 801 has an eye-facing, concave surface 812 and an objective-facing, convex surface 813 opposite the concave surface. The window 801 thus has a meniscus form. The concave surface 812 is configured to couple to the eye, either through a direct contact or through index matching material, liquid, or gel, placed in between the concave surface 812 and the eye 1.

A cone portion 803 of the patient interface 800 includes an eye attachment mechanism 804, such as a suction ring that faces the eye 1. When the suction ring 804 is in contact with the eye 1, an annular cavity 805 is formed between the suction ring and the eye. A vacuum system (not shown) comprising a vacuum tube in fluid communication with the annular cavity 805 at one end and a vacuum pump at another end, is configured to apply a vacuum within the cavity. The vacuum in the annular cavity 805 creates vacuum forces between the eye 1 and the suction ring 804 that securely attach the eye to the patient interface 800. Removing the vacuum releases or detaches the patient interface 800 from the eye 1.

With continued reference to FIGS. 3A and 3B, the cone portion 803 of the patient interface 800 also includes a cone attachment mechanism 806 that faces the cone attachment 704 of the focusing objective head 700. The cone attachment mechanism 806 and the cone attachment 704 are configured to attached together to thereby affix the position of the patient interface 800 relative to the focusing objective head 700. With the patient interface 800 affixed to the eye 1 and the focusing objective head 700 affixed to the patient interface, the position of the eye is fixed relative to the other components of the ophthalmic surgical system 1000. Attachment between the cone attachment mechanism 806 and the cone attachment 704 can be enabled by one or more of mechanical, vacuum, magnetic or other principles. For example, the cone attachment mechanism 806 may be an on/off magnet that when on attaches to a cone attachment 704 that is magnetic. Turning the magnet off releases or detaches the patient interface 800 from the cone attachment 704 of the focusing objective head 700.

Figure 4A:
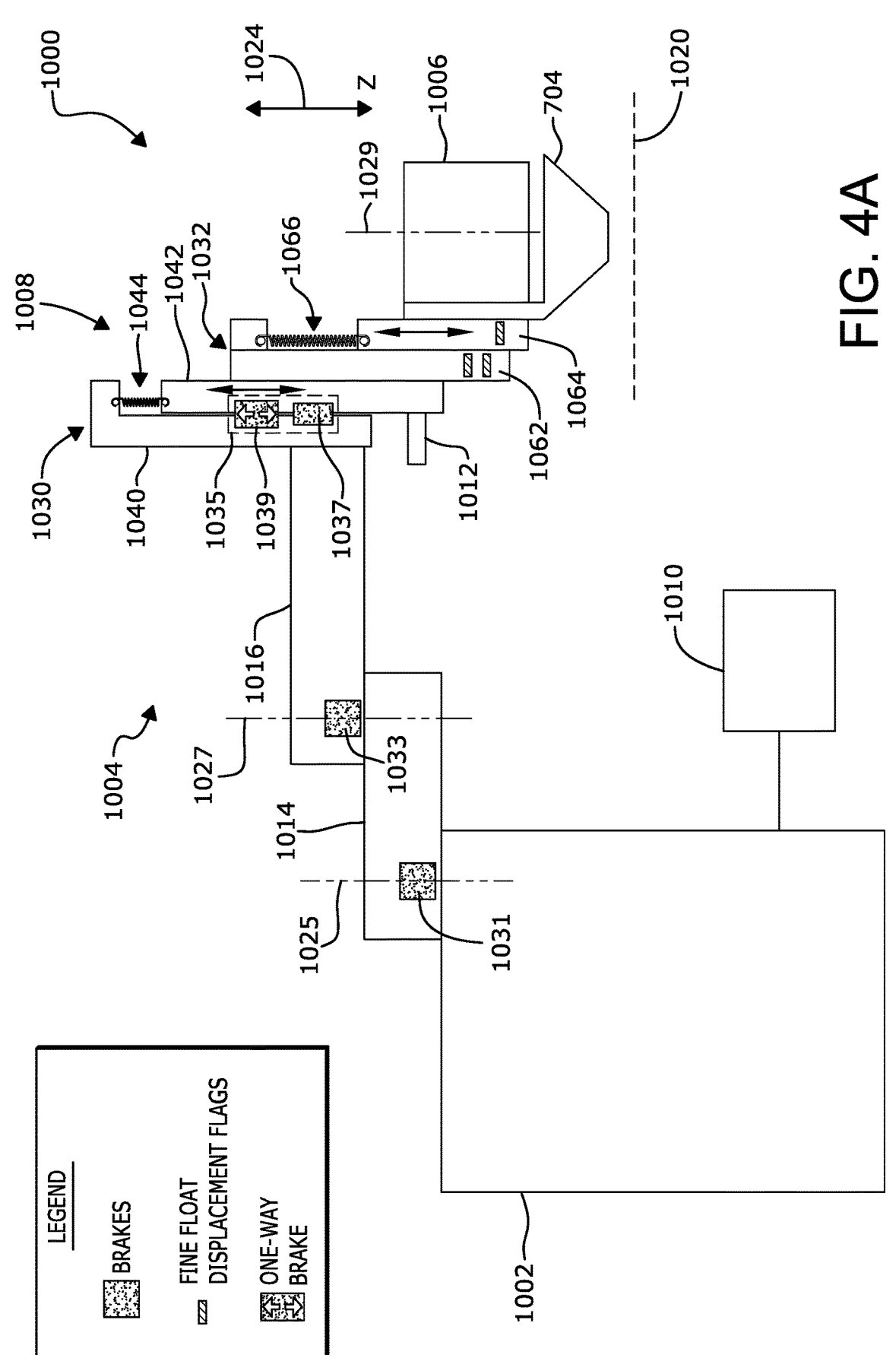
FIGS. 4A and 4B are side view (FIG. 4A) and top view (FIG. 4B) schematic illustrations of an ophthalmic surgical system having a delivery arm assembly that enables multi-dimensional (e.g., lateral and up/down) movement of the surgical head.
Figure 4B:
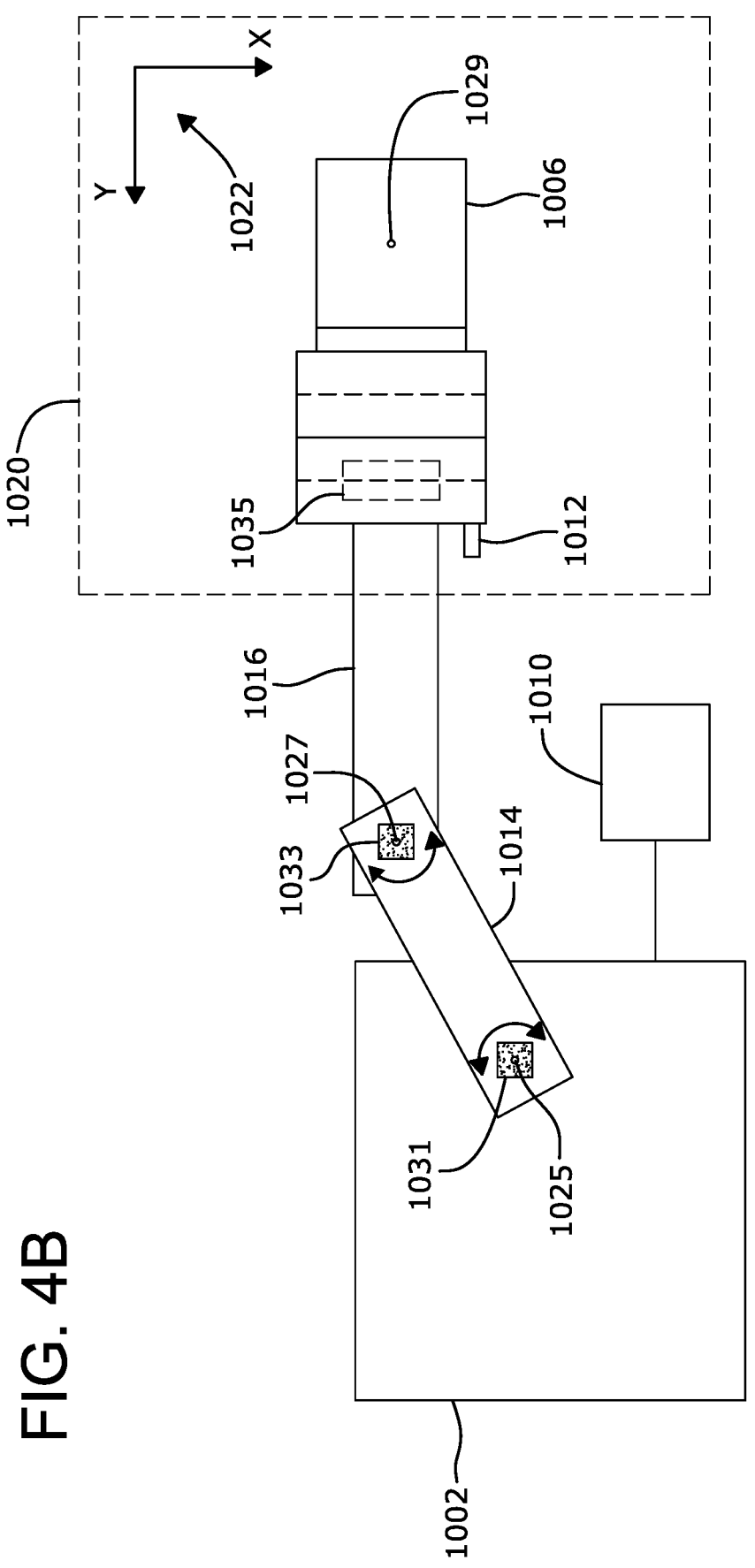

With reference to FIGS. 4A and 4B, a physical embodiment of the ophthalmic surgical system 1000 includes a chassis 1002 and a delivery arm assembly 1004, and a controller 1010. The delivery arm assembly 1004 includes a first delivery arm 1014 and a second delivery arm 1016 mechanically coupled together, a surgical head 1006, and a multistage slide mechanism 1008. The first delivery arm 1014 mechanically couples the delivery arm assembly 1004 to the chassis 1002.

Considering FIGS. 4A and 4B together with FIG. 1, the chassis 1002 of the ophthalmic surgical system 1000 contains the laser source 200, the OCT imaging apparatus 300, the visual observation apparatus 400, the dual aiming beam apparatus 450, power supply, and various other electronics, while the surgical head 1006 of the delivery arm assembly 1004 contains an optical delivery system, e.g., the beam conditioners, scanners, and combiners 500 and the beam combiners 600, and components of the focusing objective head 700. The electrical components and the optical components of the chassis 1002 and the surgical head 1006 are coupled together through the first delivery arm 1014 and the second delivery arm 1016 of the delivery arm assembly 1004. The controller 1010 includes the control system 100 and the one or more user interfaces 110. The user interfaces 110 may include, for example, a display that presents a GUI with user actuated touchscreen button, mechanical actuation buttons associated with one or more handles 1012 of the delivery arm assembly 1004, and mechanical actuation buttons associated with a foot pedal.

The mechanical actuation buttons associated with the one or more handles 1012 may enable user controlled manipulation of the delivery arm assembly 1004 and operation of other components of the ophthalmic surgical system 1000. The control buttons may include one or more brake buttons that enable lateral movement or horizontal movement and vertical movement of the surgical head 1006 of the delivery arm assembly 1004. Movement of the surgical head 1006 as such is described further below.

The operation control buttons may also include one or more actuation buttons that enable various aspects of a surgical treatment, including for example, actuation of a vacuum mechanism to secure a patient interface 800 to an eye actuation of a cone-lock mechanism to secure the patient interface to the surgical head 1006, advance of controls or settings of parameters on a graphical user interface (GUI) of the controller 1010, or activation of laser treatment.

The delivery arm assembly 1004 is operable with three degrees of motion that enable movement of the surgical head 1006 horizontally or laterally relative to a reference plane 1020 of the ophthalmic surgical system 1000, and vertically up/down relative to the reference plane. To this end, the first delivery arm 1014 of the delivery arm assembly 1004 is attached to the chassis 1002 to rotate at a first joint/coupling about a first rotation axis 1025 to provide a first degree of motion of the surgical head 1006 in a lateral plane 1022 (an x-y plane), where the lateral plane is generally parallel to the reference plane 1020 of the ophthalmic surgical system 1000. The second delivery arm 1016 of the delivery arm assembly 1004 is coupled to the first delivery arm 1014 to rotate relative to the first delivery arm at a second joint about a second rotation axis 1027 to provide a second degree of motion of the surgical head 1006 in the lateral plane. The multistage slide mechanism 1008 is mounted to the second delivery arm 1016 of the delivery arm assembly 1004 to provide a third degree of motion of the surgical head 1006 in a vertical or up/down direction 1024 (z direction) relative to a third rotation axis 1029 of the surgical head 1006. The third rotation axis 1029 is an axis about which the surgical head 1006 rotates.

The delivery arm assembly 1004 includes a lateral brake system comprising a first lateral brake 1031, a second lateral brake 1033, and a vertical brake system 1035. The lateral brake system and the vertical brake system are collectively referred to herein as the brake system. The first lateral brake 1031 is arranged and configured to prevent rotation of the first delivery arm 1014 about the first rotation axis 1025. The second lateral brake 1033 is arranged and configured to prevent rotation of the second delivery arm 1016 relative to the first delivery arm 1014 about the second rotation axis 1027. The first lateral brake 1031 and the second lateral brake 1033 work together to prevent movement of the surgical head 1006 in the lateral plane 1022 relative to the eye 1. The vertical brake system 1035 is associated with the multistage slide mechanism 1008 and is configured to prevent movement of components of the multistage slide mechanism up/down relative to the third rotational axis 1029. The vertical brake system 1035 may include either or both of a two-way brake 1037 and a one-way brake 1039.

In some embodiments, the brake system is normally "locked" to prevent motion of the delivery arm assembly 1004 in all degrees of motion and is changed to a "unlocked"

state by releasing each of the first lateral brake 1031, the second lateral brake 1033, and the vertical brake system 1035. While the brake system is in the unlocked state, motion of the delivery arm assembly 1004 in all degrees of motion is enabled. The first lateral brake 1031, the second lateral brake 1033, and the vertical brake system 1035 may be released, for example, manually by a user pressing and holding mechanical actuation buttons associated with the one or more handles 1012. To ensure safety while the brake system is released, the controller 1010 is configured to override the user activated brake button and return the brake system to the normally "locked" state in certain instances. This may occur, for example, in case of loss of electrical power to the ophthalmic surgical system 1000 during surgery. Details on brake system operation are provided later in the Brake System Operation section of this disclosure.

With continued reference to FIGS. 4A and 4B, the multistage slide mechanism 1008 includes a coarse-float counterbalance or long-range slide mechanism 1030 that is mechanically coupled to the end of the second delivery arm 1016 of the delivery arm assembly 1004. The multistage slide mechanism 1008 also includes and a short-range slide mechanism 1032 that is mechanically coupled to the long-range slide mechanism 1030.

Each of the long-range slide mechanism 1030 and the short-range slide mechanism 1032 of the multistage slide mechanism 1008 include a respective counterbalance mechanisms 1044, 1066 that offsets the apparent weight of a load mass to thereby allow for positioning of the surgical head 1006 safely over a patient where light touch contact is required. The counterbalance mechanisms 1044, 1066 are designed to float the load mass at a zero apparent weight and can be adjusted to a slightly positive or slightly negative apparent weight. While the counterbalance mechanisms 1044, 1066 are schematically illustrated as springs in FIGS. 4A and 4B, the structural configuration of the counterbalance mechanisms may be in any form, including for example, springs, pulleys, magnets, etc., or combinations thereof.

In some embodiments the long-range slide mechanism 1030 comprises a coarse backplate 1040, a coarse travel plate 1042, and the counterbalance mechanism 1044. The coarse backplate 1040 is fixed to the second delivery arm 1016 of the delivery arm assembly 1004. The coarse travel plate 1042 moves up and down relative to the coarse backplate 1040. To this end, a mechanical coupling (not shown) or mechanical guide between the coarse backplate 1040 and the coarse travel plate 1042 enables low-friction, linear movement of the coarse travel plate relative to the fixed coarse backplate. The mechanical coupling may include a ball bearing or cross-roller bearing for smooth, low friction motion of the coarse travel plate 1042 up/down relative to the coarse backplate 1040.

In some embodiments the short-range slide mechanism 1032 includes a fine backplate 1062, a fine travel plate 1064, and the counterbalance mechanism 1066. The fine backplate 1062 is fixed to and extends from the coarse travel plate 1042. The fine backplate 1062 thus moves up and down, together with the coarse travel plate 1042. The fine travel plate 1064 moves up and down relative to the fine backplate 1062. To this end, a mechanical coupling (not shown) or mechanical guide between the fine backplate 1062 and the fine travel plate 1064 enables low-friction, linear movement of the travel plate relative to the fixed plate. The mechanical coupling 1068 may include a ball bearing or cross-roller bearing for smooth, low friction motion of the fine travel plate 1064 up/down relative to the fine backplate 1062.

Figures 5A, 5B:
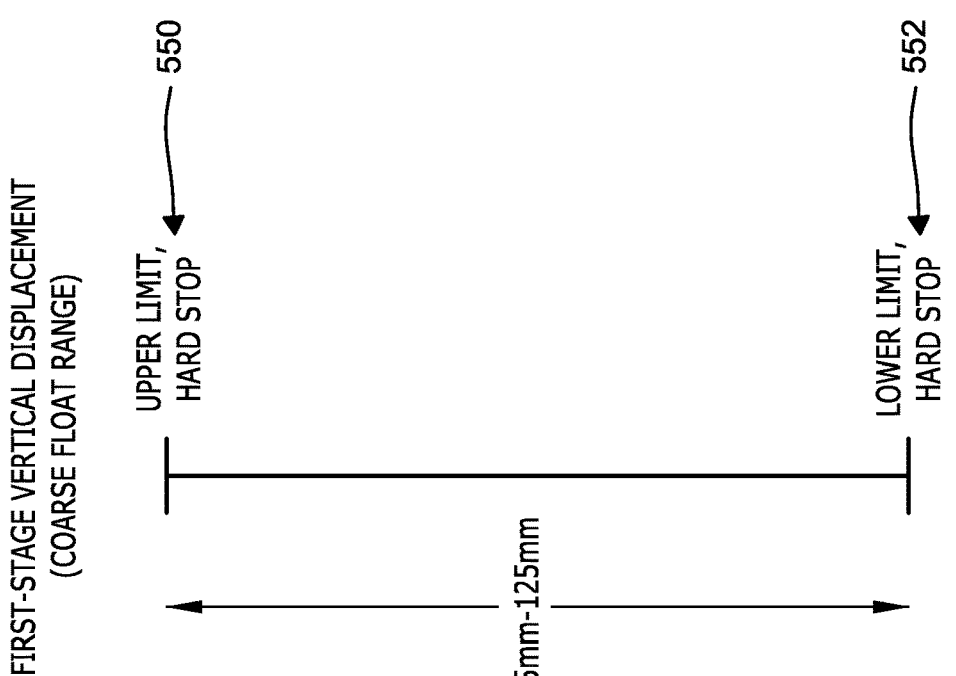
FIG. 5A is a displacement diagram for a long-range slide mechanism of a multistage delivery mechanism of the delivery arm assembly.
FIG. 5B is a displacement diagram for a short-range slide mechanism of a multistage delivery mechanism of the delivery arm assembly.

With reference to FIG. 5A, the long-range slide mechanism 1030 enables a first-stage vertical displacement of the coarse travel plate 1042, together with the short-range slide mechanism 1032 and the surgical head 1006 (which are attached to the coarse travel plate), between an upper limit 550 and a lower limit 552. The distance (or coarse float range) between the upper limit 550 and the lower limit 552 is typically in the range of 75 mm to 125 mm. The counterbalance mechanism 1044 of the long-range slide mechanism 1030 is configured to reduce the forces needed for manual positioning of the surgical head 1006. In some embodiments the counterbalance mechanism 1044 of the long-range slide mechanism 1030 is configured to provide a counterbalance force against the force of the load mass so that less than 5 Newtons (N) is required to displace or move the surgical head 1006 between the upper limit 550 and the lower limit 552.

With reference to FIG. 5B, the short-range slide mechanism 1032 is configured to enable a second-stage vertical displacement of the coarse travel plate 1042 and fine backplate 1062 relative to the fine travel plate 1064 and the surgical head 1006, between an upper limit 554 and a lower limit 556. The distance (or fine float range) between the upper limit 554 and the lower limit 556 is typically in the range of 10 mm to 60 mm. In some embodiments, the counterbalance mechanism 1066 of the short-range slide mechanism 1032 is configured to provide a counterbalance force against the force of the load mass so that the downward force on the eye 1 resulting from displacement of the surgical head 1006 toward the lower limit 556 does not exceed a pre-set level.

In some embodiments, the counterforce provided by the short-range slide mechanism 1032 is constant within the fine float range so the force on the eye is between −0.5 N and +0.5 N and does not exceed 0.5 N. In some embodiments, the counterforce provided by the short-range slide mechanism 1032 changes based on the position of the surgical head 1006 within the fine float range and the direction of travel of the surgical head. For example, the short-range slide mechanism 1032 may be configured to provide: 1) a first counterforce while the surgical head 1006 is displaced downward from the upper limit 554 to the lower limit 556, and then upward from the lower limit to a cone-activation point 558, and 2) a second counterforce while the surgical head 1006 is displaced upward from a cone-activation point 558. The first counterforce maintains the force on the eye in the range of 2 N and 3 N. This condition is referred to herein as a "heavy float" setting. The second counterforce maintains the force on the eye in the range of between −0.5 N and +0.5 N. This condition is referred to herein as a "light float" setting.

Having generally described the mechanical structure of a delivery arm assembly 1004 of a surgical system 1000, an application of the delivery arm assembly within the context of an ophthalmic surgical procedure follows.

Docking Procedure

As part of a surgical procedure, called docking, a patient interface 800 is connected and secured to the eye 1 and the cone attachment 704 of the surgical head 1006 is connected to the patient interface. The patient interface 800 is positioned between the eye 1 and the surgical head 1006 to immobilize the eye 1 relative to the ophthalmic surgical system 1000. Docking can be performed in two ways: either the patient interface 800 is connected first to the eye 1 then to the surgical head 1006, or the patient interface is connected first to the surgical head then onto the eye.

In accordance with embodiments disclosed herein, the multistage slide mechanism 1008 of the delivery arm assembly 1004 is configured to enable a docking procedure that includes a coarse motion (or long-range motion) during which the surgical head 1006 is moved toward a patient interface 800 coupled to the eye 1, followed by a fine motion (or short-range motion) during which the surgical head 1006 stops moving toward the patient interface. In one embodiment, during coarse motion the coarse travel plate 1042 of the long-range slide mechanism 1030 moves relative to the coarse backplate 1040 in a direction toward the patient interface 800. And because the short-range slide mechanism 1032 and the surgical head 1006 are attached to the coarse travel plate 1042, they also move in the direction toward the patient interface 800. The long-range motion of the surgical head 1006 brings the cone attachment 704 of the surgical head into contact with the patient interface 800.

During fine motion, when the surgical head 1006 contacts the patient interface 800 it encounters a resistive force that stops further movement of the fine travel plate 1064 in the direction toward the patient interface. Because the surgical head 1006 is attached to the fine travel plate 1064 it also stops moving in the direction toward the patient interface 800. Stoppage of the surgical head 1006 limits the force applied to the eye through the patient interface 800. However, the coarse travel plate 1042 of the long-range slide mechanism 1030 and the fine backplate 1062 of the short-range slide mechanism 1032 continue to move in a direction toward the patient interface 800.

To prevent injury, the multistage slide mechanism 1008 of the delivery arm assembly 1004 is configured to protect the eye 1 from the application of excessive forces. Ideally, the forces on the eye 1 are kept to less than 0.5 N for extended periods, and to less than 3 N for a short period of time, e.g., a few seconds. In some embodiments, the force applied to the eye 1 through the patient interface 800 after the surgical head 1006 initially contacts the patient interface is in the range of 2N to 3N and is automatically reduced to a force less than 0.5N when the surgical head couples to the patient interface.

Figure 6:
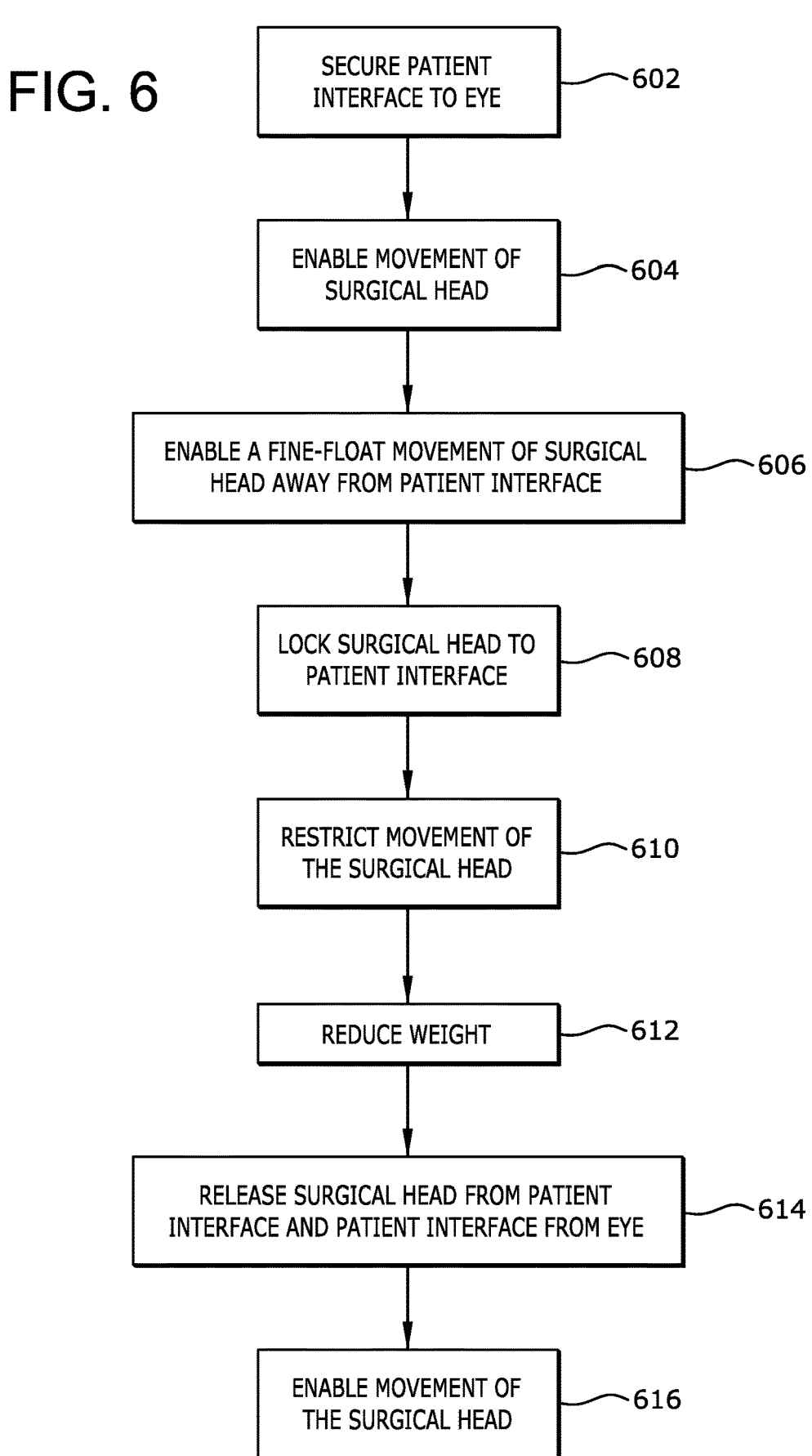
FIG. 6 is a flowchart of a method of docking a surgical head of an ophthalmic surgical system to a surgical site, e.g., an eye.

FIG. 6 is a flow chart of a method of coupling a surgical head 1006 to a surgical site, e.g., an eye 1. The method may be enabled by the surgical system 1000 of FIGS. 4A and 4B.

Figures 7A, 7B:
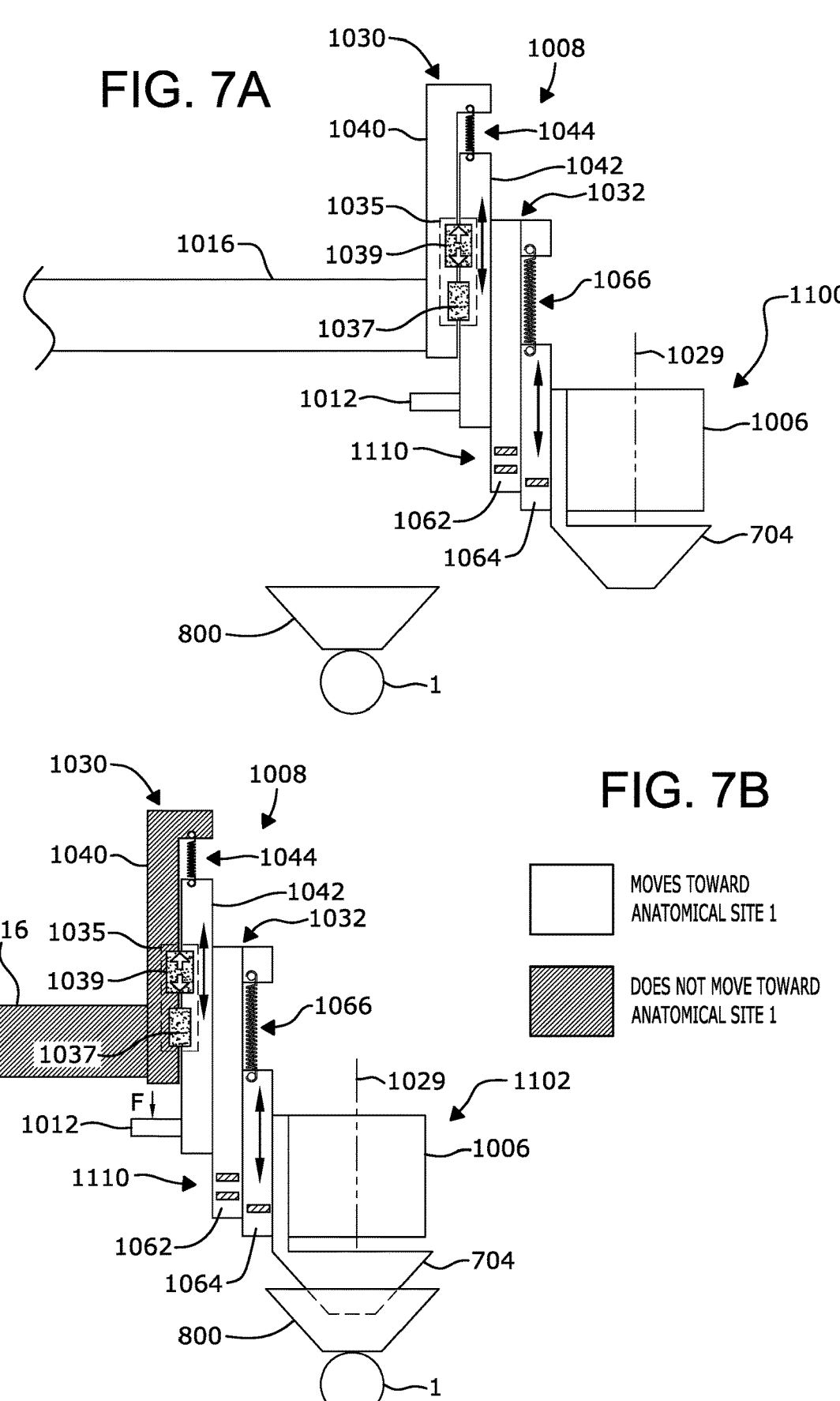
FIGS. 7A through 7E are schematic illustrations of different stages of a docking procedure enabled by the delivery arm assembly.

At block 602, and with reference to FIGS. 7A, a patient interface 800 is secured to an eye 1. For example, as described above with reference to FIGS. 3A and 3B, an eye attachment mechanism 804 mechanism in the form of a suction ring may be activated by applying suction from a vacuum to the annular cavity 805 between the ring and the eye 1 to thereby secure the patient interface to the eye. An eye suction sensor (not shown) confirms a valid coupling between the patient interface 800 and the eye 1. To this end, the eye suction sensor is configured to detect a valid by measuring negative pressure in the vacuum line or the absence of air flow from the suction ring. Conversely, a presence of air flow is indicative of separation between the suction ring and the eye, in which case the coupling between the patient interface 800 and the eye 1 is deemed invalid by the eye suction sensor.

At block 604, and with reference to FIGS. 4A, 4B, 7A, and 7B, movement of the surgical head 1006 is enabled. To this end, a brake release button on a handle 1012 may be activated to release or unlock the lateral brake system 1031, 1033 and the vertical brake system 1035 of the delivery arm assembly 1004. Releasing the lateral brake system 1031, 1033 allows pivoting of the first delivery arm 1014 and the second delivery arm 1016 of the delivery arm assembly 1004 about their respective rotation axis 1025, 1027. As such, the surgical head 1006 may be moved laterally in a lateral plane 1022 from a first location 1100 (shown in FIG. 7A) a second location 1102 (shown in FIG. 7B) that places the cone attachment 704 of the surgical head 1006 in general vertical alignment with the patient interface 800.

Figure 7C:
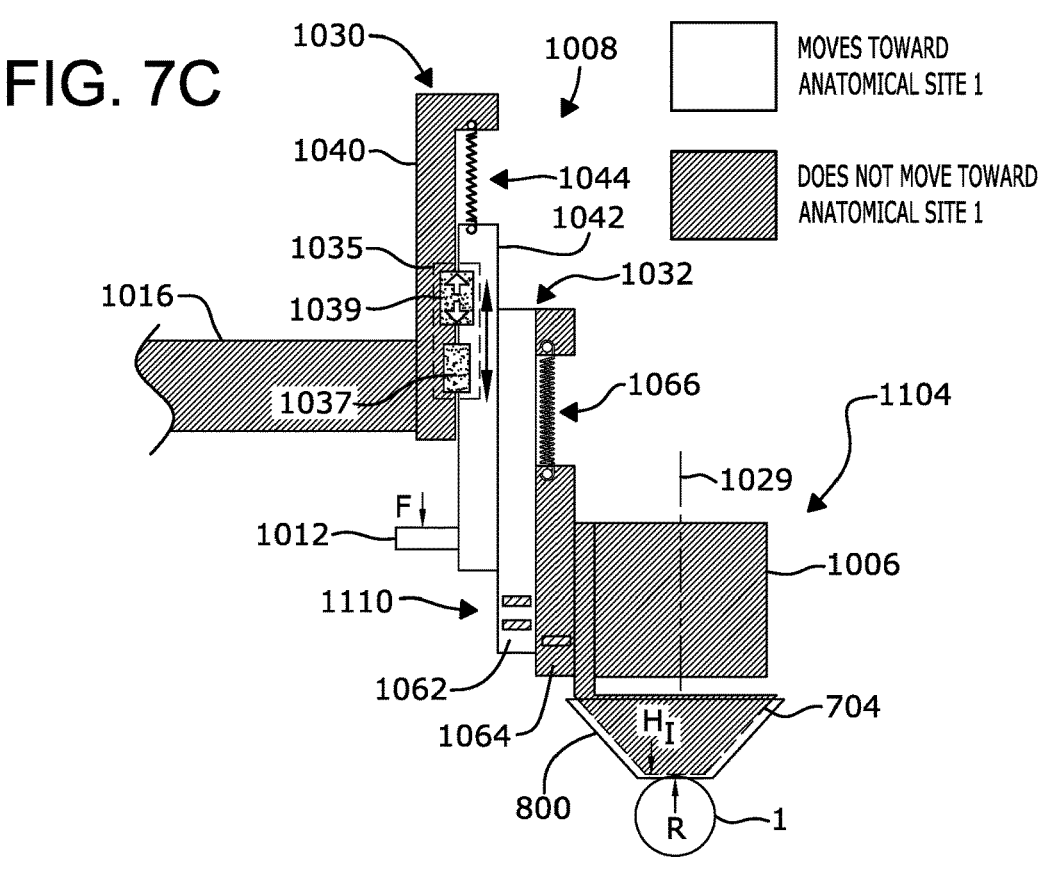

With reference to FIGS. 7B and 7C, releasing the vertical brake system 1035 allows vertical displacement of surgical head 1006 by the long-range slide mechanism 1030 toward the patient interface 800. As such, the surgical head 1006 may be moved in a z direction 1024 vertically downward from the second location 1102 (shown in FIG. 7B) to a third location 1104 (shown in FIG. 7C) to place the cone attachment 704 of the surgical head 1006 in the patient interface 800. More specifically, with reference to FIGS. 7B and 7C, the coarse travel plate 1042 of the long-range slide mechanism 1030 may slide downward relative to the coarse backplate 1040 while the counterbalance mechanism 1044 counterbalances a load mass of the counterbalance mechanism such that the displacement force needed to move the load mass either upward or downward is less than 5 N. The load mass of the counterbalance mechanism 1044 includes the surgical head 1006, the short-range slide mechanism 1032, and the coarse travel plate 1042. As previously mentioned with reference to FIG. 5A, the vertical range of motion of the coarse travel plate 1042, together with short-range slide mechanism 1032 and the surgical head 1006 at this first stage (or coarse stage) is between 75 mm and 125 mm millimeters and is referred to herein a "long range of motion. Because the short-range slide mechanism 1032 and the surgical head 1006 are attached to the coarse travel plate 1042 they move together with the coarse travel plate.

Figure 7D:
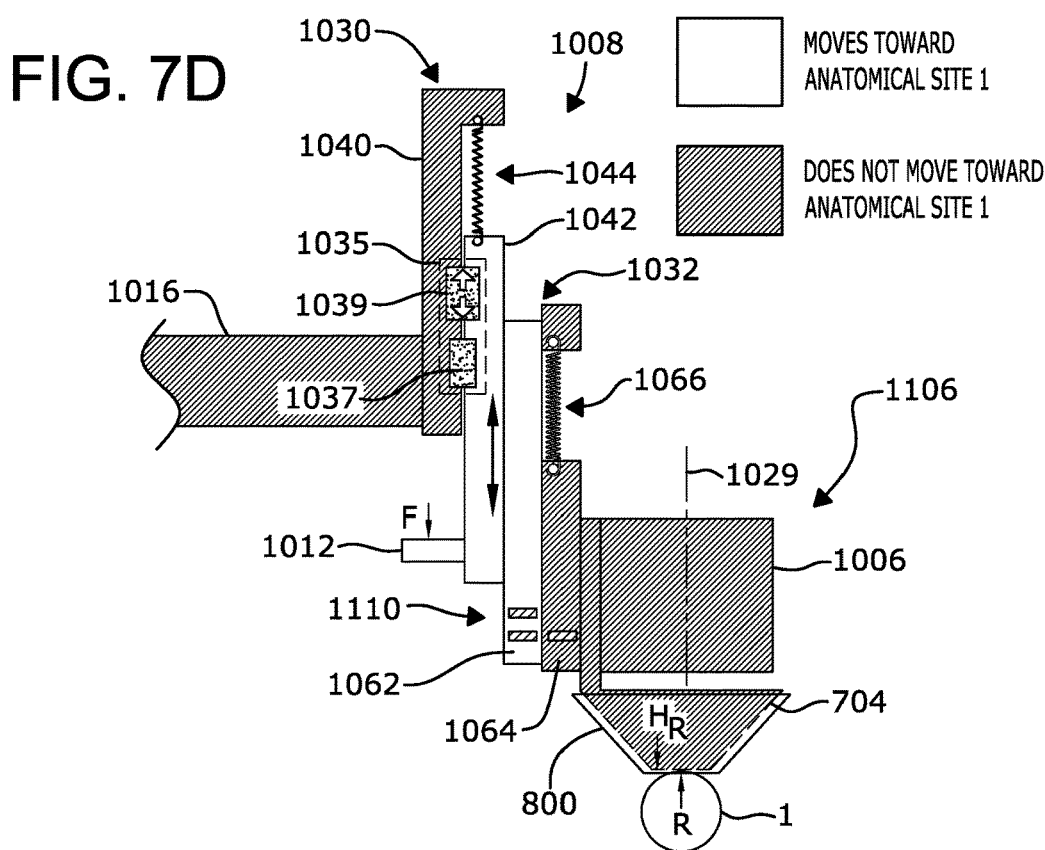

At block 606, and with reference to FIGS. 7C and 7D, a fine-float stoppage of the surgical head 1006 from further movement toward the patient interface 800 is enabled in response to the surgical head encountering a resistive force R. To this end, the lateral brake system 1031, 1033 and the vertical brake system 1035 of the delivery arm assembly 1004 may remain unlocked through continued activation of the brake release button. This allows for further movement of the surgical head 1006 by the long-range slide mechanism 1030 vertically downward relative to the patient interface 800 until the cone attachment 704 of the surgical head 1006 encounters a resistive force R at or above a threshold value through the patient interface. The resistive force R causes movement of the surgical head 1006 by the long-range slide mechanism 1030 in the z direction 1024 to stop. Regarding the resistive force R, the counterbalance mechanism 1066 of the short-range slide mechanism 1032 counterbalances a load mass of the counterbalance mechanism such that the force on the patient interface 800 (and thus the force on the eye 1) is less than 5 N. The load mass of the counterbalance mechanism 1066 includes the surgical head 1006 and the fine travel plate 1064.

Considering stoppage of the surgical head 1006 further, once the cone attachment 704 encounters a threshold resistive force R through the patient interface 800, any further attempted downward movement of the surgical head 1006 through movement of the long-range slide mechanism 1030 is stopped by the short-range slide mechanism 1032. More specifically, the fine travel plate 1064 of the short-range slide mechanism 1032 stops moving, while the coarse travel plate 1042 and the fine backplate 1062 continue to slide relative to the stopped fine travel plate 1064 and surgical head 1006 in the direction toward the patient interface 800. Thus, as shown in FIGS. 7C and 7D, the third location 1104 (shown in FIG. 7C) of surgical head 1006 is the same as the fourth location 1106 (shown in FIG. 7D), while the respective positions of the coarse travel plate 1042 of the long-range slide mechanism 1030 and the fine backplate 1062 relative to the fine travel plate 1064 are different. As previously mentioned with reference to FIG. 5B, the vertical range of motion of coarse travel plate 1042 and fine backplate 1062 relative to the fine travel plate 1064 and the surgical head 1006 at this second stage (or fine stage) is between 10 mm and 60 mm and is referred to herein a "short range of motion."

At block 608, the cone attachment 704 of the surgical head 1006 is locked in place relative to the patient interface 800—a state referred to herein as "cone lock."

In some embodiments, cone lock is automated. To this end, and with reference to FIG. 7D, the short-range slide mechanism 1032 includes a sensor 1110 (schematically shown by three displacement flags) configured to have a first activation when the surgical head 1006 is at the fourth location 1106 (shown in FIG. 7D), which position corresponds to 1508 in FIG. 5B. Stated differently, the sensor 1110 is configured to have a first activation when the relative positions of the fine travel plate 1064 (to which the surgical head 1006 is attached) and the fine backplate 1062 are as shown in FIG. 7D. This first activation is shown by the bottom alignment of the displacement flags. Upon first activation, the sensor 1110 outputs a control signal to the cone attachment mechanism 806 of the patient interface 800 that activates the cone attachment mechanism. As described above with reference to FIGS. 3A and 3B, the cone attachment mechanism 806 (e.g., a mechanical, vacuum, or magnet) secures the patient interface 800 to the cone attachment 704 of the surgical head 1006.

In some embodiments, cone lock is a manual operation. To this end, and with reference to FIG. 7D, the sensor 1110 of the short-range slide mechanism 1032 is configured to output to a display of the controller 1010 a measure of force being encountered by the cone attachment 704. The display informs the surgeon of the progress of docking. When the display indicates a force at or above a threshold force, an activation button on a handle 1012 may be activated to output a control signal to the cone attachment mechanism 806 that activates the cone attachment mechanism.

In either case of automatic operation of manual operation, a cone attachment sensor (not shown) confirms a valid coupling between the cone attachment 704 and the patient interface 800. To this end, the cone attachment sensor is configured to detect a valid coupling by measuring negative pressure in the vacuum line or the absence of airflow from the cone attachment 704. Conversely, a presence of air flow is indicative of separation between the patient interface 800 and the suction ring 806, in which case the coupling between the patient interface 800 and the eye 1 is deemed invalid by the eye suction sensor.

At block 610, movement of the surgical head 1006 is restricted or prevented. Such movement restrictions may include one or both of a restriction on vertical (up/down) movement of the surgical head 1006 by the long-range slide mechanism 1030, and a restriction on lateral movement of the surgical head by the delivery arm. Such restrictions in movement are enabled by one or more brakes.

Regarding restrictions on vertical (up/down) movement, in some embodiments, movement of the surgical head 1006 by the long-range slide mechanism 1030 may be restricted in both directions. To this end, the vertical brake system 1035 is a two-way brake 1037 configured to enter a locked state to prevent vertical movement of the surgical head 1006 through the long-range slide mechanism 1030 in both of a downward direction toward the eye 1 and an upward direction away from the eye. In some embodiments, movement of the surgical head 1006 by the long-range slide mechanism 1030 is restricted in one direction. To this end, the vertical brake system 1035 is a one-way brake 1039 configured to enter a locked state to prevent vertical movement of the surgical head 1006 through the long-range slide mechanism 1030 in a downward direction toward the eye 1 while allowing movement in an upward direction away from the eye. Details on brake system operation are provided later in the Brake System Operation section of this disclosure.

Regardless of the type of restrictions on vertical (up/down) movement of the surgical head 1006 by the long-range slide mechanism 1030, vertical movement of the surgical head by the short-range slide mechanism 1032 is not restricted. More specifically, the short-range slide mechanism 1032 does not have a brake that restricts or prevents vertical (up/down) movement of the fine travel plate 1064 (with attached surgical head 1006) relative to the fine backplate 1062. Thus, while movement of the surgical head 1006 toward the eye may be stopped when a resistive force R is encountered during docking (as shown in FIG. 7C), the short-range slide mechanism 1032 enables free upward vertical movement of the surgical head 1006. This upward movement, together with the force control effect of the counterbalance mechanism 1066, helps reduce forces on the eye 1 in cases where the patient's head or the surgical bed under the patient moves inadvertently. Sideway forces and vertical lifting forces are limited by breaking the suction coupling between the patient interface 800 and the eye 1. For this reason, the suction vacuum pressure is tuned to be just sufficient to hold the eye steady but not excessive, to allow braking of the suction force.

Figure 7E:
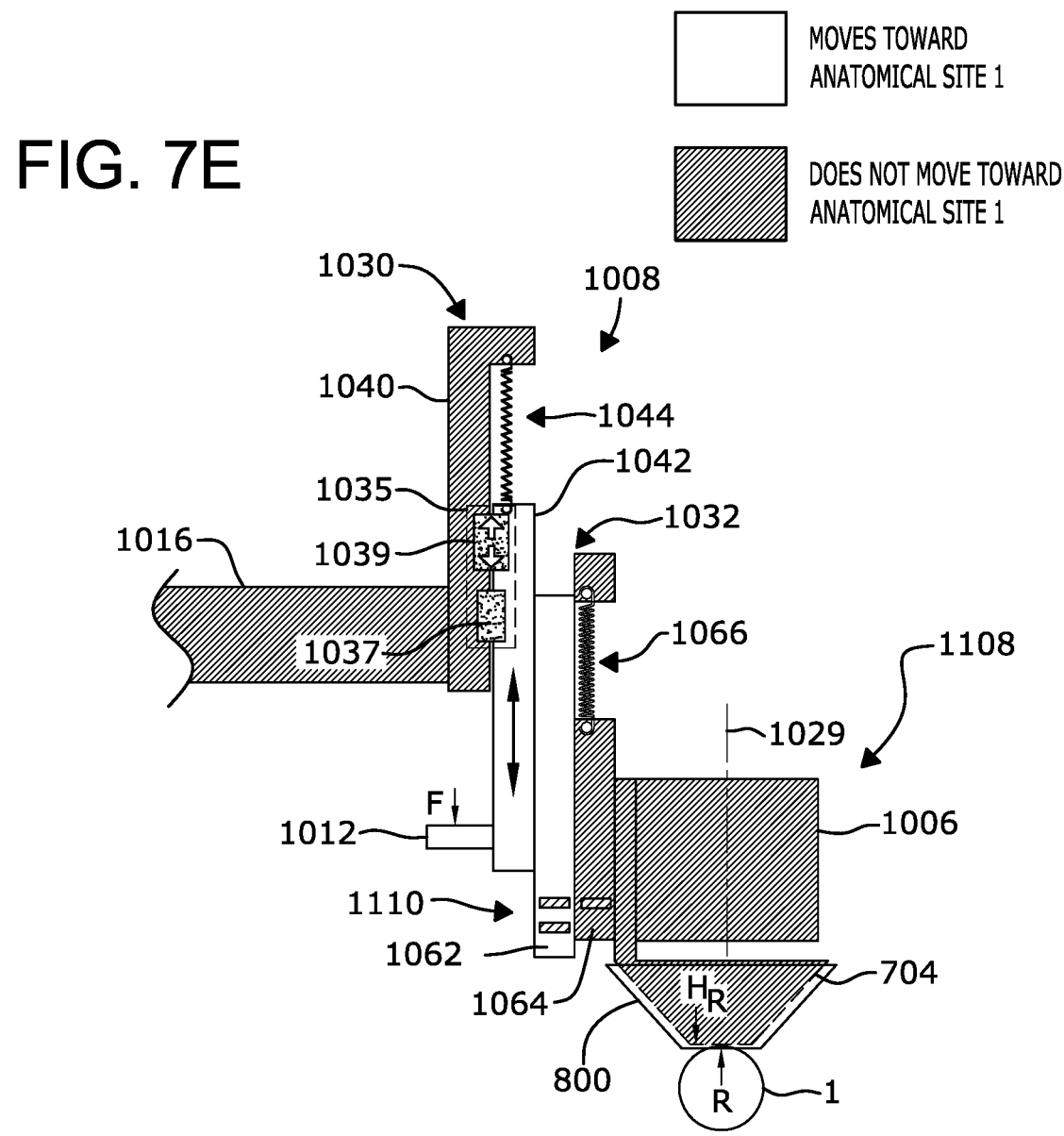

In some embodiments, restriction of movement of the surgical head 1006 by the long-range slide mechanism 1030 is automated. To this end, and with reference to FIG. 7E, the sensor 1110 is configured to have a second activation when the surgical head 1006 is at the fifth location 1108 (shown in FIG. 7E), which position corresponds to 560 in FIG. 5B. Stated differently, the sensor 1110 is configured to have a second activation when the relative positions of the fine travel plate 1064 (to which the surgical head 1006 is attached) and the fine backplate 1062 are as shown in FIG. 7E. This second activation is shown by the top alignment of the displacement flags. Upon second activation, the sensor 1110 outputs a control signal to the brake system that locks the lateral brake system 1031, 1033 and the vertical brake system 1035 of the delivery arm assembly 1004 to thereby restrict movement of the surgical head 1006.

In some embodiments, restriction of movement of the surgical head 1006 is a manual operation. To this end, and with reference to FIG. 7E, automatic locking of the lateral brake system 1031, 1033 and the vertical brake system 1035 of the delivery arm assembly 1004 by the sensor 1110 of the short-range slide mechanism 1032 may be overridden through user operation. For example, a display of the controller 1010 may indicate a cone lock state, and in response an activation button on a handle 1012 may be activated to lock the brake system. For example, if the cone lock is achieved before the second activation of the sensor 1110 the surgeon can manually lock the brake system by releasing the activation button, so the brake system assumes its normally locked state.

At block 612, the apparent weight of the surgical head 1006 is reduced. Such reduction may occur upon the first activation of the sensor 1110 described above within the context of automated cone lock. Upon first activation, the sensor 1110 outputs a control signal to a fine-float mechanism associated with the short-range slide mechanism 1032 that adjusts the counterbalance force of the short-range slide mechanism. Adjustment of the counterbalance force by the fine-float mechanism releases forces acted on the eye during the docking process. The fine float mechanism can be an additional spring, pneumatic or magnetic device configured to counterbalance the force of the short-range slide mechanism so that the force (either positive pushing down or negative pulling up) at the eye 1 is close to zero. Details of a magnetic configuration of a fine-float mechanism for adjusting counterbalance force of the short-range slide mechanism 1032 are described later with reference to FIGS. 10A, and 10B.

The fine-float counterbalance mechanism of the short-range slide mechanism 1032 functions as a variable force mechanism to provide an initially higher docking force for a portion of the docking procedure, which force is reduced as soon as cone lock is achieved. This reduction in force minimizes the duration that a heavier downward pressure is applied to the eye 1. The initial higher pressure, applied for a few seconds, helps achieving a more dependable contact between the cone attachment 704 and the inside surface of the patient interface 800 achieve cone lock. Once cone lock is achieved the weight of the fine float on the eye can be reduced.

At block 614, upon completion of the laser treatment, the surgical head 1006 is released from the patient interface 800 and patient interface is released from the eye 1. To this end, the eye attachment mechanism 804 and the cone attachment mechanism 806 are deactivated manually or automatically by the controller 1010. In some embodiments, the cone attachment 704 may include a mechanical actuator arranged and configured to push down on the cone attachment to break surface tension forces in between the upper surface of the window 801 of the patient interface 800 and a mating glass surface of the surgical head 1006.

At block 616, movement of the surgical head 1006 is enabled. To this end, a brake release button on a handle 1012 may be activated to release or unlock the lateral brake system 1031, 1033 and the vertical brake system 1035 of the delivery arm assembly 1004. This allows for movement of the surgical head 1006 away from the eye 1. As a safety feature for undocking, a second sensor, e.g., displacement or force sensor, associated with the short-range slide mechanism 1032 can detect excessive negative force on the eye 1 and output a control signal that locks the vertical brake system 1035 to prevent upward movement of the surgical head 1006 by the long-range slide mechanism 1030 before the eye 1 is decoupled from the surgical head 1006. The sensor may also output a control signal that deactivates either or both of the eye attachment mechanism 804 mechanism and the cone attachment mechanism 806 of the patient interface 800 to thereby decouple the surgical head 1006 from the eye. After the eye 1 is decoupled from the surgical head 1006, the vertical brake system 1035 may be unlocked to enable upward movement of the surgical head 1006 by the long-range slide mechanism 1030.

Regarding deactivation of the eye attachment mechanism 804, which secures the patient interface 800 to the eye 1, such deactivation and resulting decoupling between the patient interface and eye may be confirmed by the surgical system 1001 prior to unlocking the vertical brake system 1035. In one embodiment, deactivation is facilitated and confirmed by applying a burst of positive pressure into the eye attachment mechanism 804, e.g., suction ring, and sensing a positive air flow indicative of separation between the eye 1 and the suction ring.

Regarding deactivation of the cone attachment mechanism 806, which secures the patient interface 800 to the cone attachment 704, such deactivation and resulting decoupling between the patient interface and eye may be confirmed by the surgical system 1001 prior to unlocking the vertical brake system 1035. In one embodiment, deactivation is facilitated and confirmed by applying a burst of positive pressure into the cone attachment mechanism 806, e.g., suction ring, and sensing a positive air flow indicative of separation between the patient interface 800 and the suction ring.

Figure 8A:
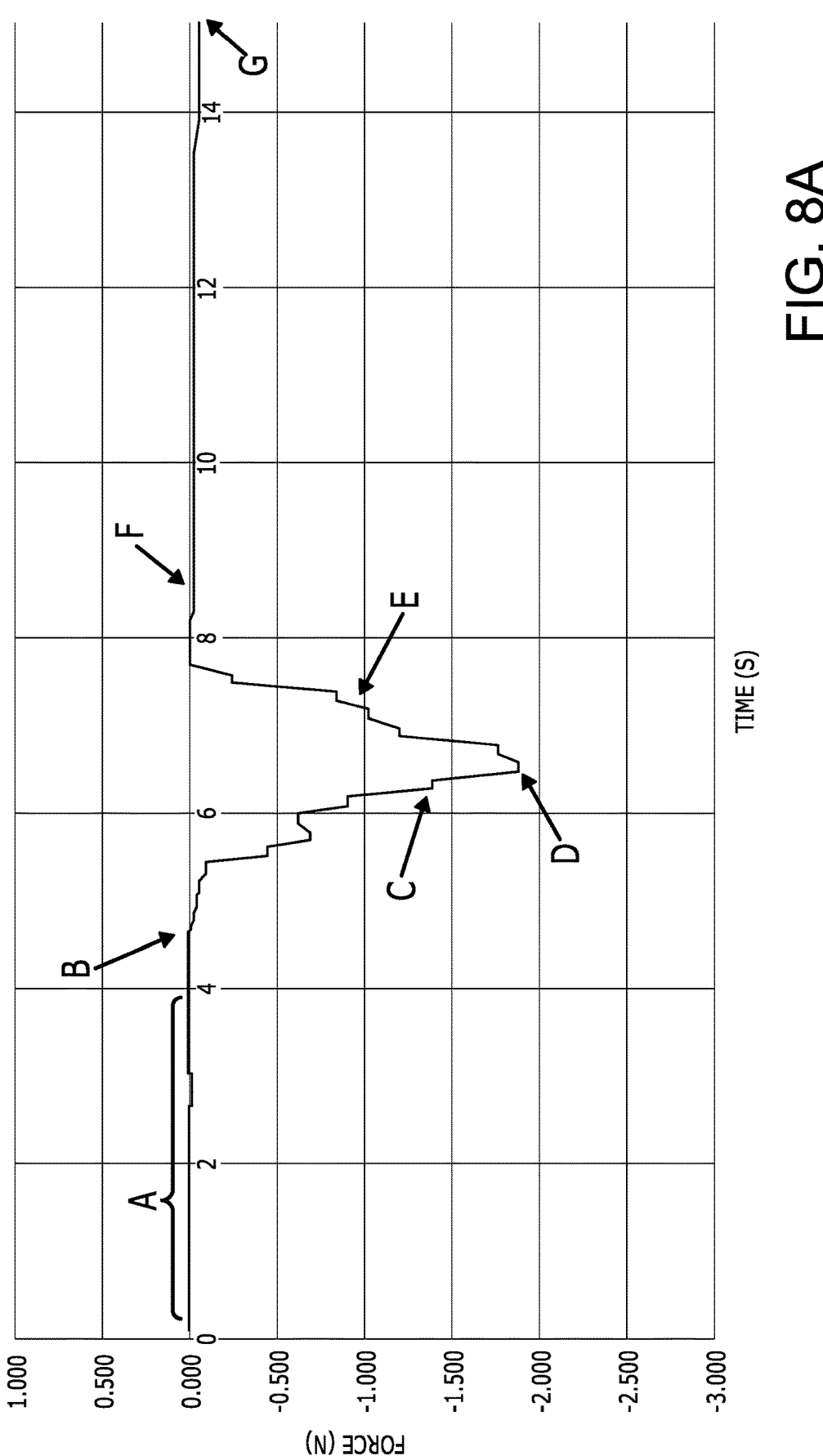
FIGS. 8A and 8B are graphs showing changes in force on an eye at different times during the docking procedure of FIG. 6.
Figure 8B:
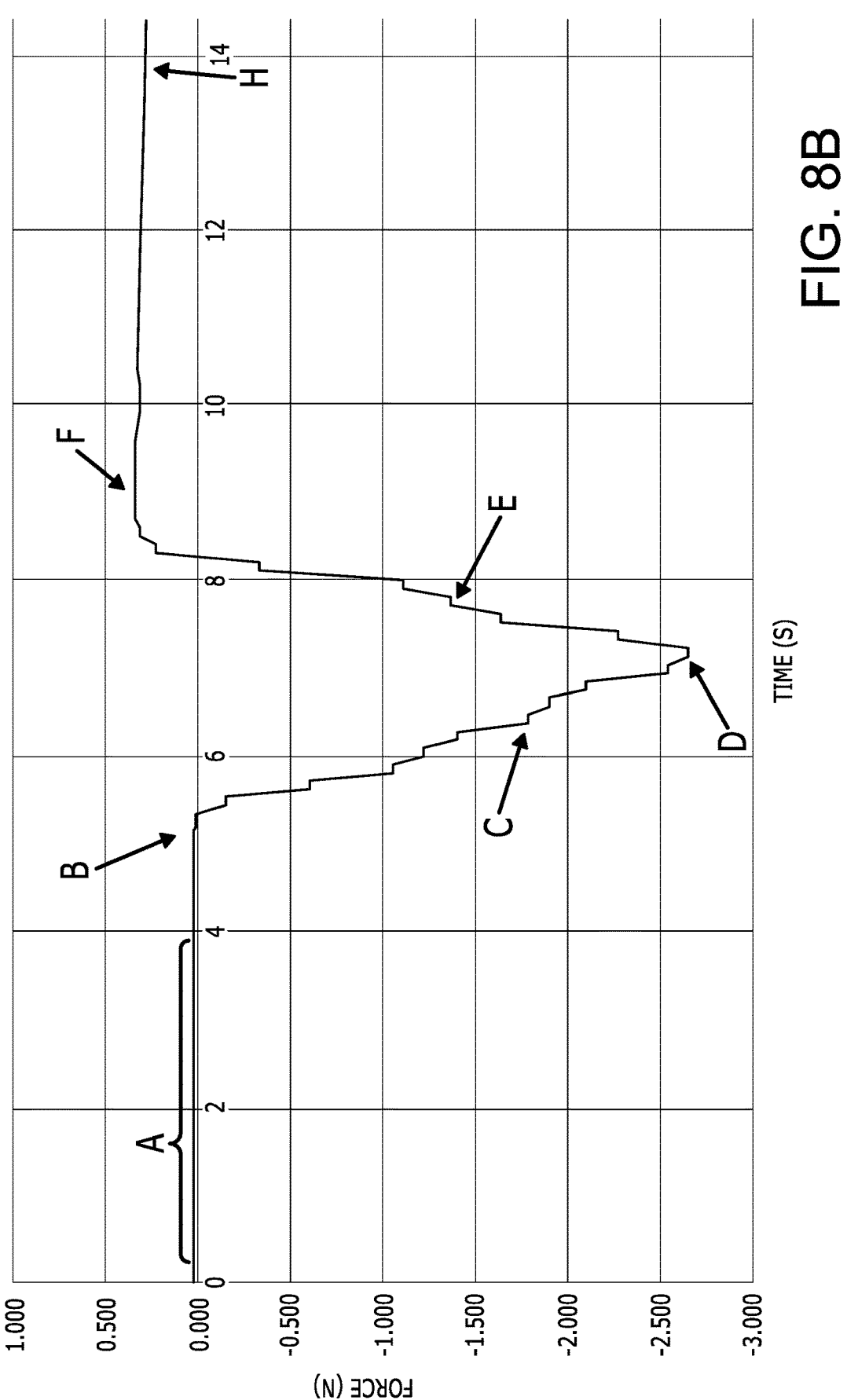

With reference to the graphs of FIGS. 8A and 8B, during a docking procedure by a surgical system 1000 configured in accordance with embodiments disclosed herein, the force applied to a surgical site, e.g., eye, can be controlled so as to reduce to near zero N upon docking completion. The graphs of FIGS. 8A and 8B show downward force on the eye during docking tests on model eyes. The graphs show zero N force prior to docking, forces in between 2 N and 3 N for a few seconds during docking, a stop to the increase of force, and then a reduction of the force to below 0.5 N.

Considering graphs of FIGS. 8A and 8B further, during period A the docking procedure has not yet started and the force on the eye 1 is near zero N.

Between point B (start of docking procedure) and point C (initial engagement of cone attachment 704 with patient interface 800) the downward force on the eye 1 increases. At point C, the counterbalance mechanism 1066 of short-range slide mechanism 1032 limits the force on the eye 1 to less than –2 N.

At point D, cone lock is activated, and the brake system is locked to prevent further downward movement of the surgical head 1006 by the long-range slide mechanism 1030. This restriction on movement of the surgical head 1006 prevents further increase in the force on the eye 1.

Between point D and point F, the downward force on the eye 1 decreases. During this time, at point E the counterbalance mechanism 1066 of short-range slide mechanism 1032 adjusts to limit the force on the eye 1 to less than 0.5 N. At point F, the counterbalance mechanism 1066 of short-range slide mechanism 1032 limits the force on the eye 1 to near zero N.

At point G (in FIG. 8A), a residual force in the direction of the eye 1 may be applied to the eye after docking due to mechanical tolerances associated with the counterbalance mechanism 1066 of short-range slide mechanism 1032. At point H (in FIG. 8B), a residual force opposite the direction of the eye 1 may be applied to the eye. This residual force pulls the eye 1 upward.

Multistage Slide Mechanism

Figure 9A:
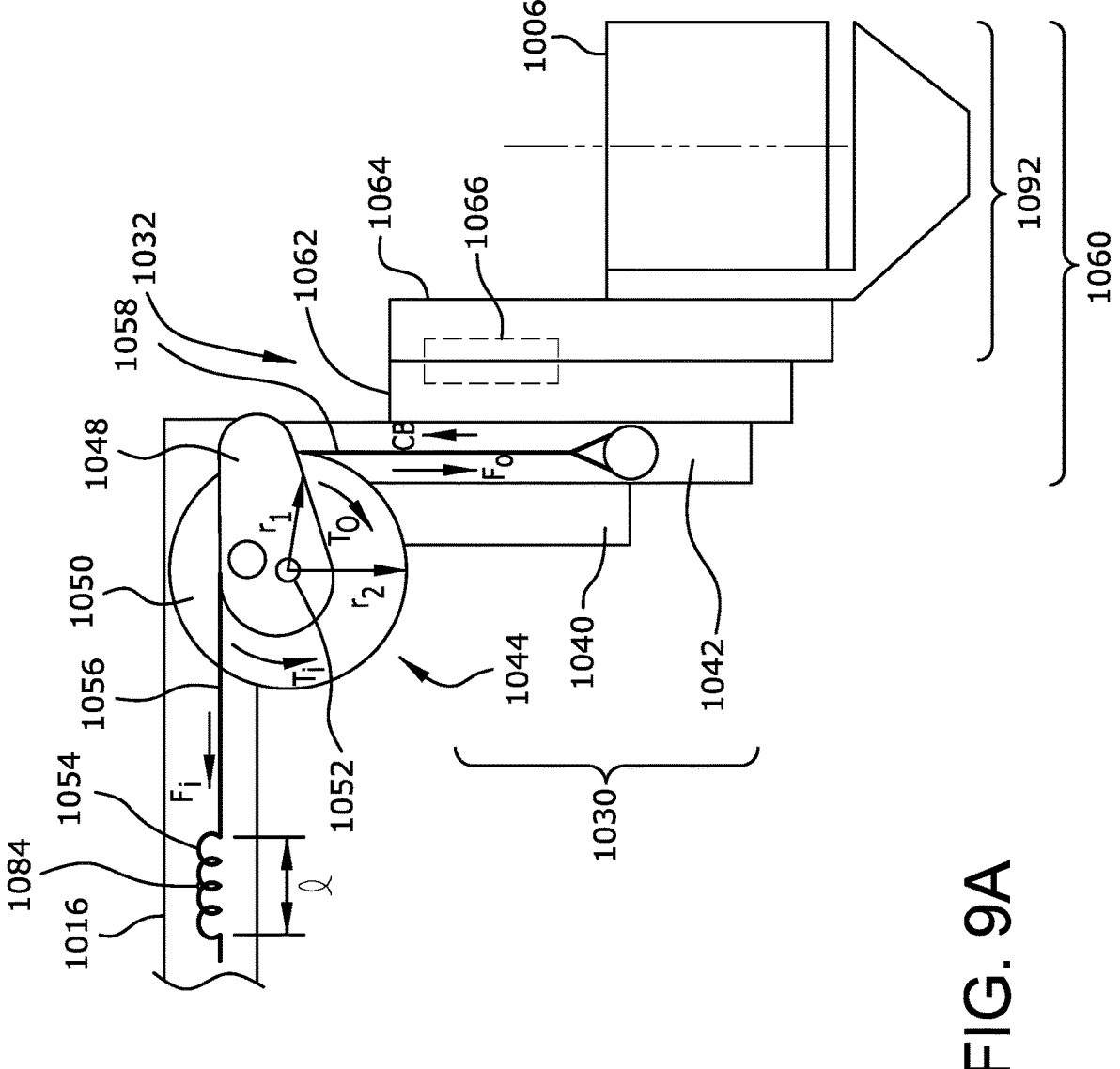
FIGS. 9A and 9B are side view (FIG. 9A) and top view (FIG. 9B) schematic illustrations of a configuration of a multistage delivery mechanism having a pulley-based long-range slide mechanism and a magnetic short-range slide mechanism.
Figure 9B:
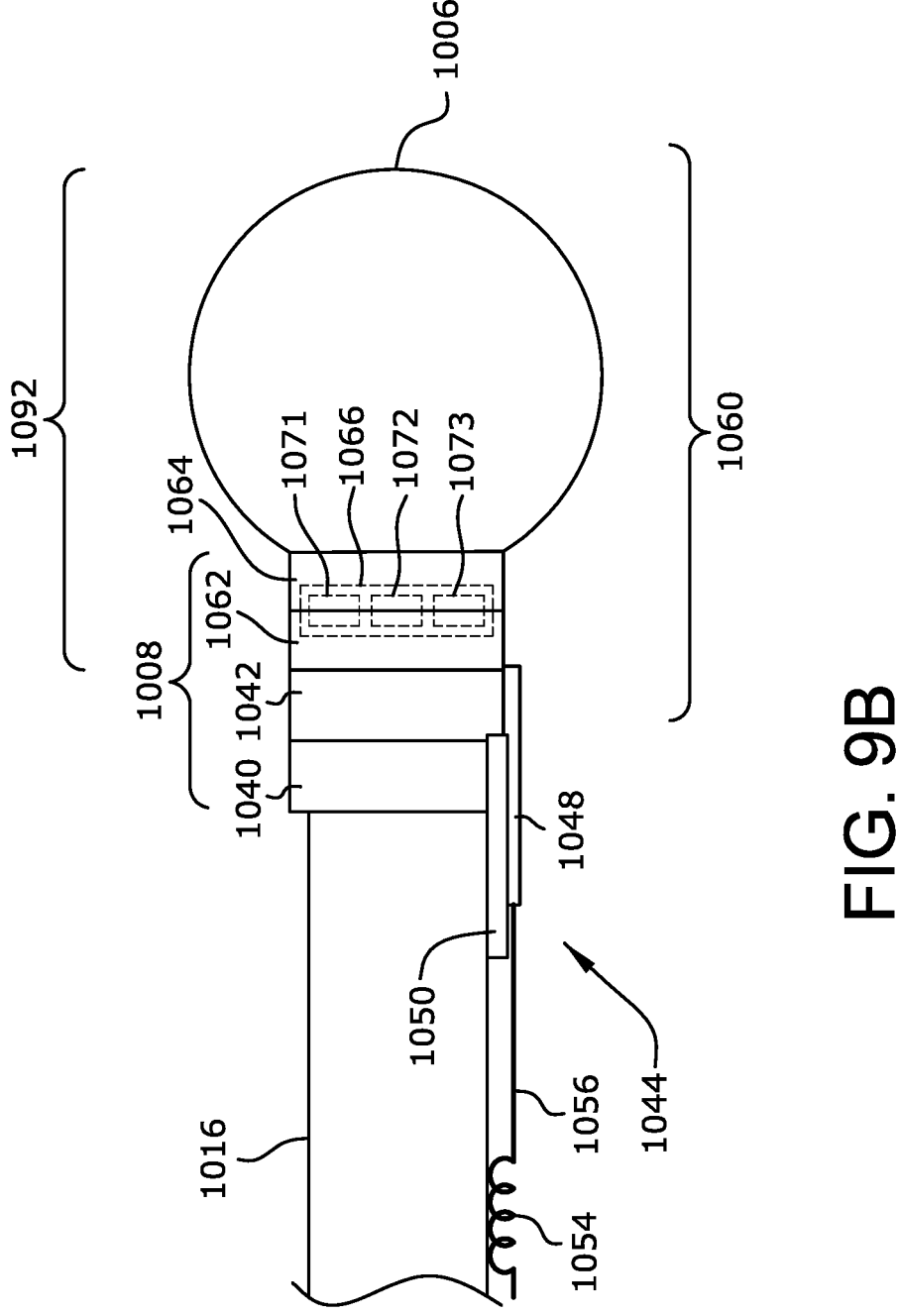

With reference to FIGS. 9A and 9B, in some embodiments the multistage slide mechanism includes a long-range slide mechanism 1030 having a pulley counterbalance mechanism 1044, and a short-range slide mechanism 1032 having a magnetic counterbalance mechanism 1066. The pulley counterbalance mechanism 1044 is also referred to herein as a coarse-float counterbalance, while the short-range slide mechanism 1032 is also referred to as a fine-float counterbalance.

Pulley Counterbalance Mechanism

With continued reference to FIGS. 9A and 9B, in some embodiments the pulley counterbalance mechanism 1044 may include a variable-radius input pulley 1048 and a constant-radius output pulley 1050 coupled together about a common bearing 1052. An input spring 1054 (extension or compression) having a length l is coupled to an input cable 1056 that attaches to and wraps around the variable-radius input pulley 1048. An output cable 1058 is attached to and wraps around the constant-radius output pulley 1050 and is coupled to a load mass 1060 of the pulley counterbalance mechanism 1044. The load mass 1060 of the pulley counterbalance mechanism 1044 includes the surgical head 1006, the short-range slide mechanism 1032, and the coarse travel plate 1042.

The variable-radius input pulley 1048 and the constant-radius output pulley 1050 rotate coaxially about the common bearing 1052 and are held in fixed rotational phase with one another. As the load mass 1060 moves up/down, the input cable 1056 spins the variable-radius input pulley 1048 as the output cable 1058 is wrapped about or unwrapped from the output side of the variable-radius input pulley. This causes subsequent wrapping/unwrapping of the input cable 1056 that changes the length l of the input spring 1054, and the input force $F_i$ generated by the input spring scales as:

$$F_i = k \cdot x$$

where k is the spring constant of the input spring 1054, and x is the change in length l of the input spring.

To achieve a constant output force $F_o$ at the load mass 1060, one or both of the radius $r_1$ of the variable-radius input pulley 1048 and the radius $r_2$ of the constant-radius output pulley 1050 varies. The input cable 1056 and the output cable 1058 pull tangent respectively to the variable-radius input pulley 1048 and the constant-radius output pulley 1050, generating a torque about the common bearing 1052. To counterbalance the load mass 1060, the input torque $T_i$ generated by the tangent pull of the input cable 1056 equals the output torque $T_o$ generated by the tangent pull of the output cable 1058. The torque can be held constant by scaling the pulley radii according to the spring constant based on the relation:

$$F = k \cdot x = T/r$$

where k is the spring constant of the input spring 1054, x is the change in length l of the input spring, T is the required torque, and r is the virtual radius of the pulley perpendicular to the tangent line of action of the cable. Either the radius $r_1$ of the variable-radius input pulley 1048, the radius $r_2$ of the constant-radius output pulley 1050, or the rotational phase of the two pullies relative to each other can be varied to achieve a constant counterbalancing force CB, or a variable counterbalancing force governed by either a linear spring rate different than that of the input spring 1054, or a nonlinear spring rate.

The pulley counterbalance mechanism 1044 provides a counterbalancing force CB that lifts the load mass 1060 through pulley bearings and cable bending. The pulley bearings and cable bending are the primary sources of friction associated with the pulley counterbalance mechanism 1044 (apart from the mechanical coupling between the coarse backplate 1040 and the coarse travel plate 1042). As a result, friction and hysteresis are low. The pulley counterbalance mechanism 1044, with its cables 1056, 1058 wrapped around pulleys 1048, 1050 that spin on high precision bearings, provides smooth motion that behaves like a mass counterbalance, but without the inconvenience of bulky masses.

The pulley counterbalance mechanism 1044 is configured to enable adjustment of the counterbalance force CB. To this end, an adjustable spring tensioner 1084 associated with the input spring 1054 allows preload setting according to the load mass 1060. Once adjusted to the desired counterbalance force CB, the counterbalance force remains constant.

Magnetic Counterbalance Mechanism

With reference to FIGS. 9A and 9B, in some embodiments the magnetic counterbalance mechanism 1066 includes a set of magnetic couplings coupled to a load mass 1092 of the magnetic counterbalance mechanism. The set of magnetic couplings may include one, two, three, or more magnetic couplings. The magnetic counterbalance mechanism 1066 provides a counterbalancing force CB to the load mass 1092 without physically contacting the load mass. As a result, friction and hysteresis are minimal, there is no physical wear of the coupled components (e.g., the magnetic counterbalance mechanism 1066 and the loas mass), and no debris is generated by the moving parts.

The load mass 1092 of the magnetic counterbalance mechanism 1066 includes the surgical head 1006 and the fine travel plate 1064. In one configuration, the set of magnetic couplings include a first magnetic coupling 1071, a second magnetic coupling 1073, and an intermediate magnetic coupling 1072. Each of the magnetic couplings 1071, 1072, 1073 includes a fine-travel magnet positioned between a pair of ferromagnetic metal plates. The fine-travel magnets are mechanically coupled to the fine travel plate 1064 while the pair of metal plates are mechanically coupled to the fine backplate 1062, which in turn is coupled with the coarse travel plate 1042.

Figure 10A:
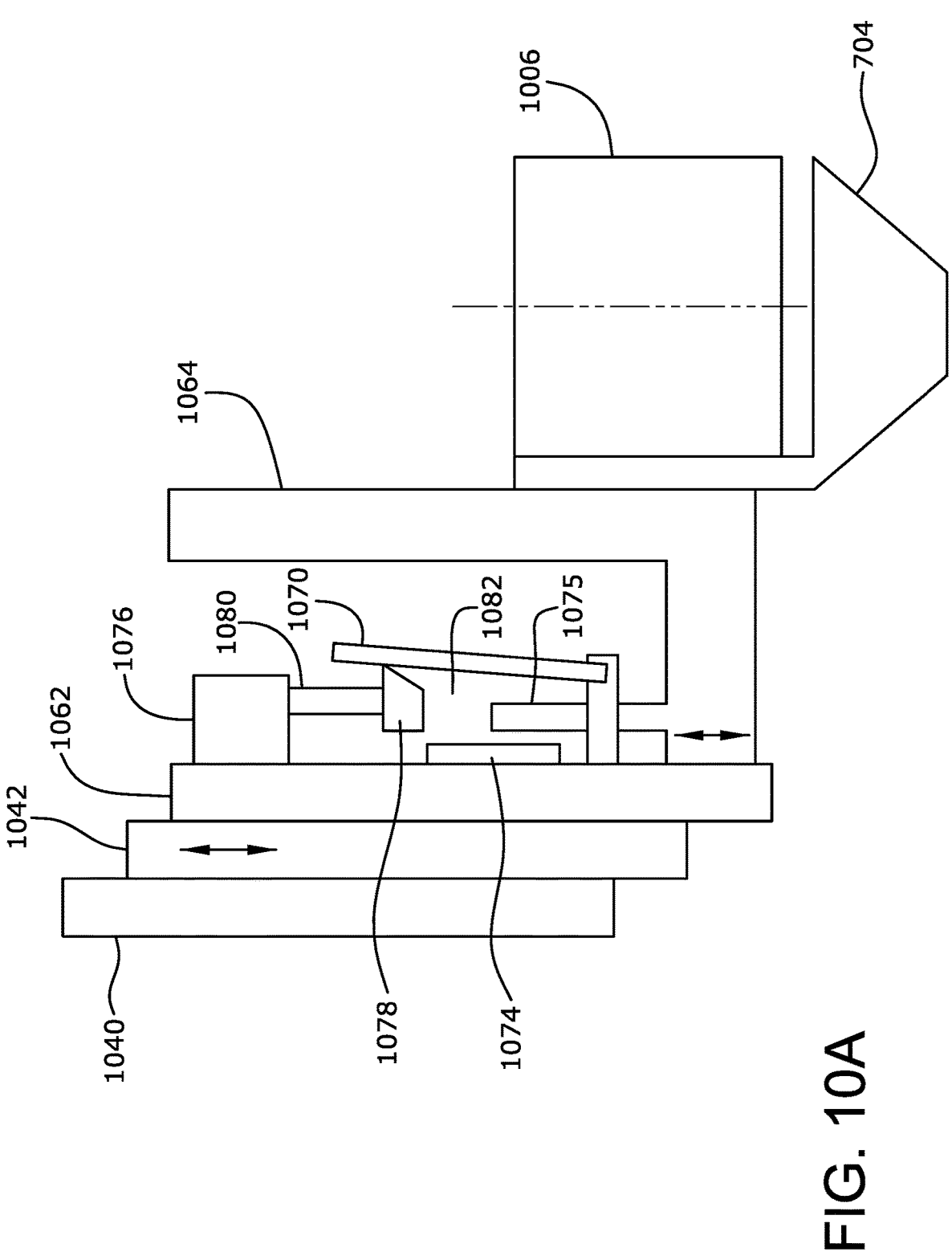
FIGS. 10A and 10B are schematic illustrations of a multistage delivery mechanism showing components of a magnetic fine-float counterbalance mechanism in a first state (FIG. 10A) and a second state (FIG. 10B).
Figure 10B:
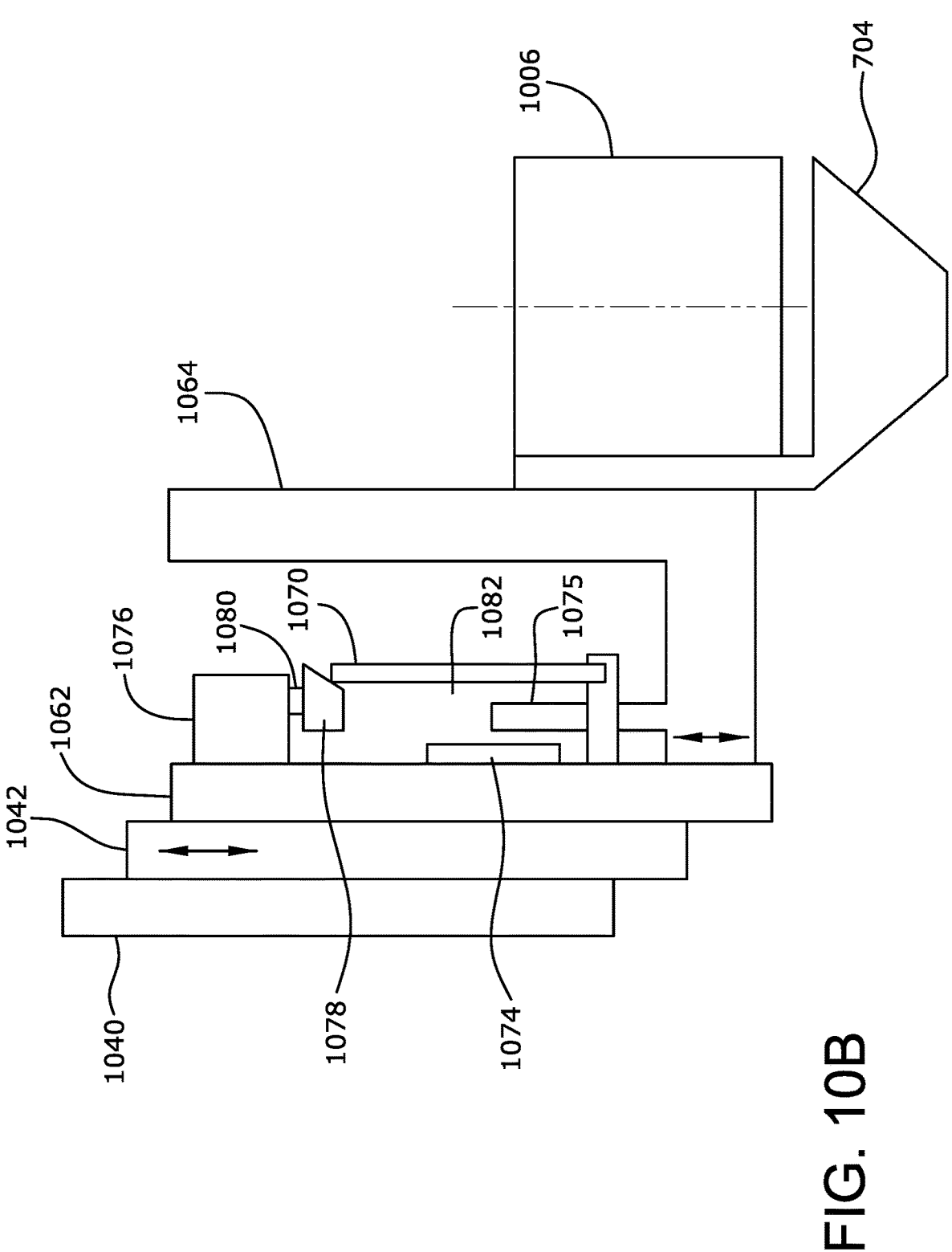

With reference to FIGS. 10A and 10B, the intermediate magnetic coupling 1072 of the magnetic counterbalance mechanism 1066 is configured to adjust the counterbalance weight of the load mass 1092. The intermediate magnetic coupling 1072 includes an intermediate fine-travel magnet 1075 that is mechanically coupled to the load mass 1092 through the fine travel plate 1064. The intermediate magnetic coupling 1072 is positioned between a pair of metal plates that include a magnetic pivot plate 1070 and a fixed plate 1074 that are mechanically coupled to the fine backplate 1062, which in turn is coupled with the coarse travel plate 1042.

The intermediate fine-travel magnet 1075 is a permanent magnet that is magnetized through its thickness, such that the magnet is much longer in the direction perpendicular to its magnetic pole orientation. The magnetic pivot plate 1070 is shorter in length than the intermediate fine-travel magnet 1075. Thus, when the magnetic pivot plate 1070 is placed near the long end of the intermediate fine-travel magnet 1075, the magnetic pivot plate is attracted to the surface of the fine-travel magnet, as well as to the center position along the length of the magnet. If the magnetic pivot plate 1070 is held apart from the intermediate fine-travel magnet 1075, the force pulling the magnetic pivot plate to the fine-travel magnet's long axis center generates an approximately constant force in that direction.

The counterbalance force CB provided by the magnetic counterbalance mechanism 1066 is governed by controlling an air gap 1082 between the magnetic pivot plate 1070 and the intermediate fine-travel magnet 1075. The air gap 1082 between the magnetic pivot plate 1070 and the intermediate fine-travel magnet 1075 may be adjusted to increase or decrease the counterbalance force of the magnetic counterbalance mechanism 1066, against the force of the load mass 1092. The magnetic counterbalance mechanism 1066 is modular in that it may be configured with multiple magnets in parallel or varied magnet strength, which can be mix and match to achieve a desired counterbalance lifting force.

The magnetic counterbalance mechanism 1066 also includes a wedge motor assembly that is configured to adjust the size of the air gap 1082 between the intermediate fine-travel magnet 1075 and the magnetic pivot plate 1070.

The wedge motor assembly includes a motor 1076 and a wedge 1078 that is coupled to a rod 1080 that extends from the motor. The apparent weight of the load mass 1092 can be set to one of a number of calibrated set points using an electronically controlled actuator that operates the motor 1076 to move the wedge 1078 up/down to thereby adjust the size of the air gap 1082. If fully continuous control of apparent weight of the load mass 1092 is desired, the electronically controlled actuator can be paired with a load sensor to measure the instantaneous weight of the load mass and adjust the air gap 1082 in real time.

In accordance with embodiments disclosed herein, the magnetic counterbalance mechanism 1066 is configured to transition between a "heavy" mode and a "light" mode by changing the size of the air gap 1082. In the heavy mode, the size of the air gap 1082 is greater than the size of the gap in light mode. The larger air gap 1082, while in heavy mode, results in a smaller counterbalance force against the load mass 1092 comprising the surgical head 1006. Thus, the apparent weight of the load mass 1092 is heavier and the downward force applied to the eye 1 is greater. Conversely, the smaller air gap 1082, while in light mode, results in a greater counterbalance force against the load mass 1092 comprising the surgical head 1006. Thus, the apparent weight of the load mass 1092 is lighter and the downward force applied to the eye 1 is less. In one configuration, the weight applied to the eye 1 is in in the range of 100 g to 300 g when the magnetic counterbalance mechanism 1066 is in heavy mode, and in the range of −100 g to +100 g when the magnetic counterbalance mechanism 1066 is in light mode.

As disclosed above, the intermediate magnetic coupling 1072 includes structures arranged to provide an air gap 1082 that can be adjusted to set the apparent weight of the load mass 1092. While the structures in the embodiment of FIGS. 10A and 10B include a pair of metal plates and an intermediate magnet, other configurations are contemplated. For example, the air gap 1082 may be defined by a pair of spaced apart magnets, or a metal plate spaced apart from a magnet.

Control System

Figure 11:
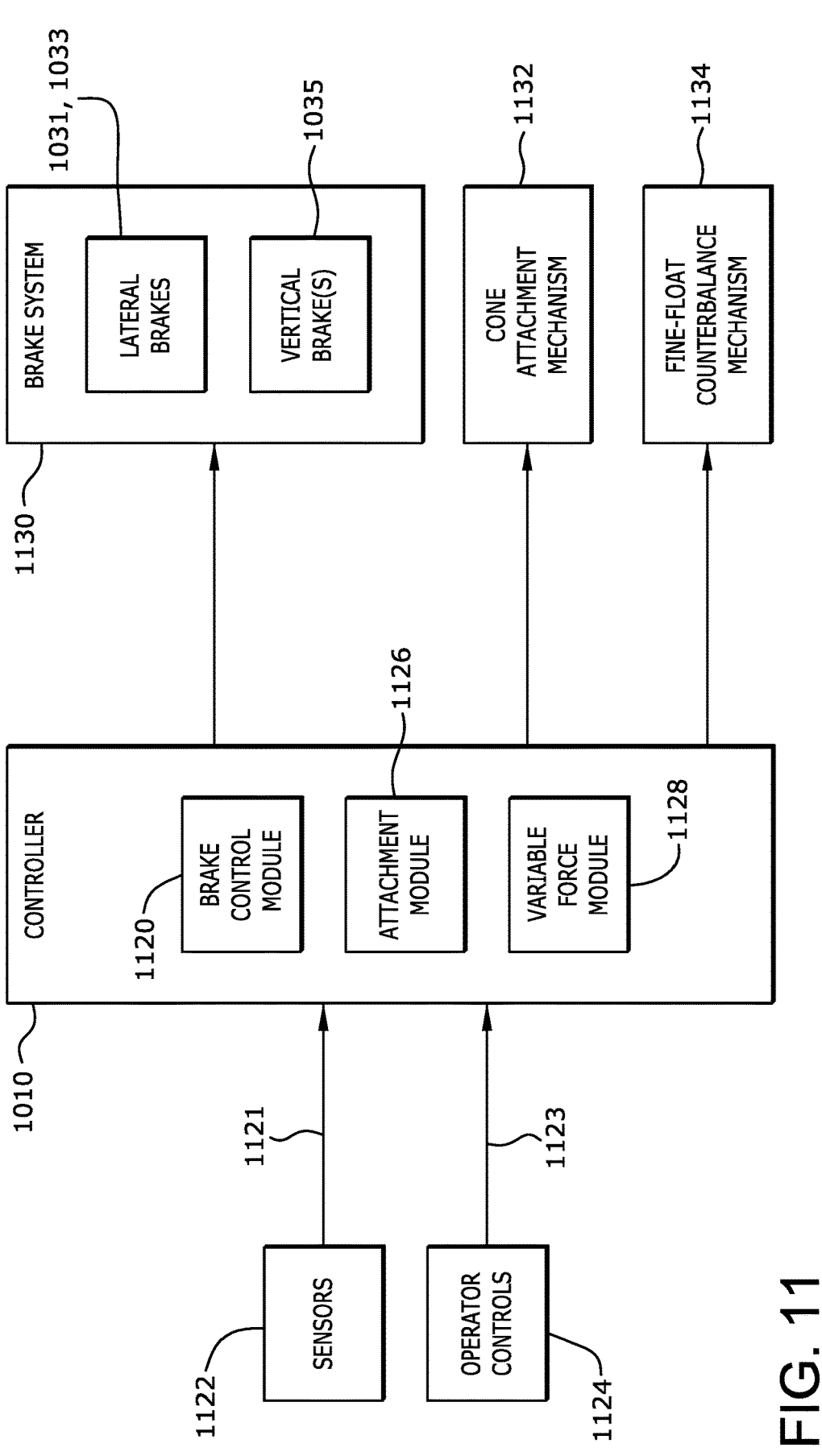
FIG. 11 is a block diagram of a control system of an ophthalmic surgical system.

With reference to FIG. 11, features of the surgical system 1000 during a docking procedure are controlled by a controller 1010 based on sensor signals 1121 from one or more sensors 1122 and control signals 1123 from one or more operator controls 1124. The controller 1010 includes a brake control module 1120, an attachment module 1126, and a variable force module 1128. The brake control module 1120 includes program logic that processes the signals 1121, 1123 to determined how to set the state (locked or unlocked) of one or more of the first lateral brake 1031, the second lateral brake 1033, and the vertical brake system 1035 of the brake system 1130. The attachment module 1126 includes program logic that processes the signals 1121, 1123 to determine the cone-lock state (on/off) of the cone attachment mechanism 1132. The variable force module 1128 includes program logic that processes the signals 1121, 1123 to determined how to set the mode (heavy/light) of the fine-float counterbalance mechanism 1134.

The sensors 1122 may include the sensor 1110 associated with the short-range slide mechanism 1032. As described with reference to FIGS. 7D and 7E, this sensor 1110 may be displacement sensor that provides sensor signals 1121 indicative of the position of the fine travel plate 1064 relative to the fine backplate 1062. Because the surgical head 1006 is attached to and moves with the fine travel plate 1064, these sensor signals 1121 are also indicative of the position of the surgical head relative to the eye 1. These sensor signals 1121 may also be indicative of positive and negative forces at the eye 1. The displacement sensor 1110 may have a mechanical configuration (e.g., limit switches, mechanical flags, levers, etc.), an electromagnetic configuration (e.g., a Hall effect sensor), an optical configuration, or any other known configuration.

In some embodiments, the displacement sensor 1110 also functions as a force sensor. In this case, the sensor signals 1121 provided by the sensor 1110 may be correlated with force measurements at the cone attachment 704 of the surgical head 1006, which in turn correlate with forces applied at the eye 1 through the cone attachment. These forces at the eye 1 may be positive, downward forces applied to the eye, or negative, upward pulling forces applied to the eye. Negative and positive force measurements can be obtained by measuring displacements of the fine travel plate 1064 of the short-range slide mechanism 1032 based on the force-displacement curve of the fine travel plate 1064. This curve may be measured and set to a desired shape during the manufacturing and calibration process by adjusting the balancing springs and/or balancing magnets of the short-range slide mechanism 1032.

Sensor signals 1121 from the displacement sensor 1110 are provided to the brake control module 1120 where they are processed by program logic to determine whether the controller 1010 should lock either or both of the lateral brake system 1031, 1033 and the vertical brake system 1035. An example of brake control is disclosed above at block 610 of FIG. 6, wherein movement of the surgical head 1006 is restricted based on a displacement sensor 1110. In some embodiments, the brake control module 1120 is configured to determine the direction of movement of the surgical head 1006 based on changes in sensor signals 1121 corresponding to changes in position of the surgical head over time. The brake control module 1120 may determine whether the controller 1010 should lock either or both of the lateral brake system 1031, 1033 and the vertical brake system 1035 based on the direction of movement. For example, the controller 1010 may control the state of a one-way brake 1039 to unlock the brake for the allowed direction and lock the brake for the prohibited direction.

Sensor signals 1121 from the displacement sensor 1110 are provided to the attachment module 1126 where they are processed by program logic to determine whether the controller 1010 should set the cone attachment mechanism 1132 on or off. An example of cone attachment control is disclosed above at block 608 of FIG. 6, wherein cone attachment is turned on based on a displacement sensor 1110. Considering cone attachment control further, the displacement sensor 1110 may be configured to output a sensor signal 1121 that causes the controller 1010 to activate cone lock based on a position of the fine travel plate 1064 relative to the fine backplate 1062 that corresponds to threshold weight or force on the eye. The threshold force for cone lock activation may be set between 0.1 N and 0.4 N for the cone lock activation. Note that in some embodiments the cone lock usually triggers at a low value, for example at 0.15 N and the force on the eye does not experience forces larger than this value.

Sensor signals 1121 from the displacement sensor 1110 are also provided to the variable force module 1128 where they are processed by program logic to determine whether the controller 1010 should set the fine-float counterbalance mechanism 1134 to light mode or heavy mode. Logic operations of the variable force module 1128 are described below in the "Variable Force Control" section.

The sensors 1122 may include an eye suction sensor configured to confirm activation and deactivation of a valid coupling between a patient interface 800 and an eye 1. In one embodiment, the eye suction sensor is configured to measure the vacuum pressure or the absence of air flow from the eye attachment mechanism 804. In another embodiment, the eye suction sensor is configured to apply a burst of positive pressure into an eye attachment mechanism 804, e.g., suction ring, of the patient interface 800, sense air flow through the eye attachment mechanism, and output a sensor signal indicative of the air flow.

Sensor signals 1121 from the eye attachment sensor are provided to the attachment module 1126 where they are processed to determine the suction state (on/off) of the eye attachment mechanism 804. For example, a sensor signal 1121 from the eye attachment sensor that represents a negative air flow is indicative of valid, secure coupling between the suction ring 804 and the eye 1, while a sensor signal that represents a positive air flow is indicative of separation between the suction ring and the eye.

Other types of sensors may be used to confirm activation and deactivation of a valid coupling between a patient interface 800 and an eye 1. For example, a weight sensor positioned at the contact interface between the patient interface 800 and the eye 1 may be configured to sense a threshold weight or force on the eye.

The sensors 1122 may include cone attachment sensor configured to confirm activation and deactivation of a valid coupling between a cone attachment 704 of a surgical head 1006 and a patient interface 800. In one embodiment a sensor measures the negative air pressure applied to the cone attachment mechanism 806. In another embodiment, the cone attachment sensor is configured to apply a burst of positive pressure into a cone attachment mechanism 806, e.g., suction ring, of a patient interface 800, sense air flow through the cone attachment mechanism, and output a sensor signal indicative of the air flow.

Sensor signals 1121 from the cone attachment sensor are provided to the attachment module 1126 where they are processed to determine the cone-lock state (on/off) of the cone attachment mechanism 1132. For example, a sensor signal 1121 from the cone attachment sensor that represents a negative air flow is indicative of valid, secure coupling between the patient interface 800 and the suction ring 806, while a sensor signal that represents a positive air flow is indicative of separation between the patient interface and the suction ring.

Other types of sensors 1122 may be used to provide sensor signals 1121 that confirm activation and deactivation of a valid coupling between a cone attachment 704 of a surgical head 1006 and a patient interface 800. For example, a weight sensor positioned at the contact interface between an exterior surface of the cone attachment 704 relative to an interior of the patient interface 800 may be configured to sense a weight or force on the patient interface and provide a sensor signal 1121 indicative of the sensed weight or force to the attachment module 1126, where the sensed weight or force is compared to a threshold weight or force to determine the state of coupling between a cone attachment 704 of a surgical head 1006. As another example, a position sensor may be arranged relative to the cone attachment 704 and an interior of the patient interface 800 and configured to sense the position of an exterior surface of the cone attachment relative to the interior of the patient interface and provide a sensor signal 1121 indicative of the sensed position to the attachment module 1126, where the sensed position is compared to a threshold to determine the state of coupling between a cone attachment 704 of a surgical head 1006.

Sensor signals 1121 from the cone attachment sensor are also provided to the brake control module 1120, where they are processed by program logic to determine whether the controller 1010 should lock either or both of the lateral brake system 1031, 1033 and the vertical brake system 1035. In some embodiments, a sensor signal 1121 indicative of a valid coupling between the cone attachment 704 and the patient interface 800 causes the controller 1010 to lock the lateral brake system 1031, 1033 to prevent lateral movement of the surgical head 1006, and to lock the vertical brake system 1035 to prevent both positive, downward forces on the eye 1 and negative, upward pulling forces at the eye.

The operator controls 1124 may include the previously described brake release button that may be activated by an operator to output a control signal 1123 indicative of a pressed state or released state of the button. The control signals 1123 are provided to the brake control module 1120, where they are processed by program logic to determine whether the controller 1010 should release or unlock the lateral brake system 1031, 1033 and the vertical brake system 1035 of the delivery arm assembly 1004. Note, a brake release initiated through an operator control 1124 may be overridden by a sensor signal 1121 originating from a sensor 1122.

Variable Force Control

The variable force module 1128 includes program logic that determines whether to set the fine-float counterbalance mechanism 1134 to light mode or heavy mode. As previously described, in the light mode the apparent weight of a load mass comprising the head 1006 is less than the apparent weight while in the heavy mode. In some embodiments, logic of the variable force module 1128 sets the fine-float counterbalance mechanism 1134 to light mode (light weight) when one or more of the following conditions exist: 1) an absence of a control signal 1123 indicative of a brake release; 2) a sensor signal 1121 from the cone attachment sensor indicative of a valid coupling between the head 1006 and the patient interface 800; and 3) a sensor signal 1121 from the eye attachment sensor indicative of a valid coupling between the patient interface 800 and the anatomical site 1.

In some embodiments, logic of the variable force module 1128 sets the fine-float counterbalance mechanism 1134 to heavy mode (heavy weight) when one or more of the following conditions exist: 1) an absence of a control signal 1123 indicative of a brake release; 2) a sensor signal 1121 from the cone attachment sensor indicative of an invalid coupling between the head 1006 and the patient interface 800; and 3) a sensor signal 1121 from the eye attachment sensor indicative of an invalid coupling between the patient interface 800 and the anatomical site 1.

Brake System

As described above with reference to FIGS. 4A and 4B, the surgical system 1000 includes a brake system having a first lateral brake 1031, a second lateral brake 1033, and a vertical brake system 1035. The first lateral brake 1031 is arranged and configured to prevent rotation of the first delivery arm 1014 about the first rotation axis 1025. The second lateral brake 1033 is arranged and configured to prevent rotation of the second delivery arm 1016 relative to the first delivery arm 1014 about the second rotation axis 1027. The first lateral brake 1031 and the second lateral brake 1033 work together to prevent movement of the surgical head 1006 in the lateral plane 1022 relative to the eye 1. The vertical brake system 1035 is associated with the multistage slide mechanism 1008 and is configured to prevent movement of components of the multistage slide mechanism up/down relative to the third rotational axis 1029, and thus prevent movement of the surgical head 1006 in a z direction 1024. The vertical brake system 1035 may include either or both of a two-way brake 1037 and a one-way brake 1039.

In general, the brake system is configured to transition between a locked state and an unlocked state. The brake system is in a normally locked state, during which lateral movement of the surgical head 1006 through the delivery arm assembly 1004 is prevented by locking the first lateral brake 1031 and the second lateral brake 1033, and up/down movement of the surgical head through the long-range slide mechanism 1030 is prevented by locking the vertical brake system 1035. In the unlocked state, lateral movement of the surgical head 1006 through the delivery arm assembly 1004 is enabled by releasing the first lateral brake 1031 and the second lateral brake 1033, and movement of the surgical head through the long-range slide mechanism 1030 is enabled by releasing the vertical brake system 1035.

More specifically regarding the vertical brake system 1035, in the case of a two-way brake 1037 in the unlocked state, the movement of the surgical head 1006 through the long-range slide mechanism 1030 is enabled in both directions, up/away from and down/toward the eye 1. In the case of a one-way brake 1039, in the unlocked state, the movement of the surgical head 1006 through the long-range slide mechanism 1030 is enabled in the direction up/away from the eye 1 and is prevented in the direction down/toward the eye.

Considering the vertical brake system 1035 further, as previously disclosed the vertical brake system may include either or both of a two-way brake 1037 and a one-way brake 1039. A one-way brake 1039, in particular a fully mechanical one-way brake, configured to operate in parallel with the two-way brake 1037 may serve as a back-up safety device, mitigating against malfunction of sensors 1122, the brake control module 1120, or against operator error.

The two-way brake 1037 is configured to transition between a locked state, during which vertical movement of the surgical head 1006 through the long-range slide mechanism 1030 is prevented in both the downward direction toward the eye 1 and the upward direction away from the eye; and an unlocked state, during which vertical movement of the surgical head 1006 through the long-range slide mechanism 1030 is allowed in both the downward direction toward the eye 1 and upward direction away from the eye.

The one-way brake 1039 is configured to transition between a two-way unlocked state, and a one-way unlocked state. In the two-way unlocked state, vertical movement of the surgical head 1006 through the long-range slide mechanism 1030 is allowed in both a downward direction toward the eye 1 and an upward direction away from the eye. In the one-way unlocked state, vertical movement of the surgical head 1006 through the long-range slide mechanism 1030 is prevented in the downward direction toward the eye 1 but allowed in the upward direction away from the eye. In a vertical brake system 1035 having both a two-way brake 1037 and a one-way brake 1039, the one-way brake overrides the two-way brake in the unlocked state to prevent movement of the surgical head 1006 in the downward direction toward the eye 1.

Considering the one-way brake 1039 further, it provides a safety feature by limiting or preventing downward movement of the surgical head 1006 toward the eye 1 at different stages of a docking procedure and during the surgical procedure, while allowing upward movement away from the eye. For example, after the surgical head 1006 is locked to the patient interface (FIG. 6, block 608), placing the one-way brake 1039 in an unlocked state prevents further downward force on the eye 1, while simultaneously allowing for upward movement of the surgical head away from the eye in case of patient movement. As another example, in cases where the cone attachment 704 is not properly aligned with the patient interface 800 such that the cone lock sensor does not detect a valid coupling between the cone attachment and the patient interface, placing the one-way brake 1039 in a one-way unlocked state prevents movement of the surgical head 1006 toward the eye. For example, without the one-way brake 1039 a user may apply excessive force on the eye 1 in an attempt to properly align and couple the cone attachment 704 with the patient interface 800.

The one-way brake 1039 may be an electro-mechanical brake or a mechanical brake.

An example electro-mechanical one-way brake 1039 may be a conventional two-way brake that is configured to be set to one of a two-way locked state or a one-way unlocked state. Setting of the starting setpoint of one-way brake activation for an electro-mechanical one-way brake may be achieved by adjusting the operation of a displacement sensor 1110. In one configuration, a displacement sensor 1110 may be set so that the force level that activates the one-way brake is around 0.6 N.

Example mechanical one-way brake 1039 include a mechanical friction mechanism, and a ratchet consisting of a linear rack equipped with asymmetric teeth and a pawl engaging with the teeth.

Figures 12A, 12B, 12C:
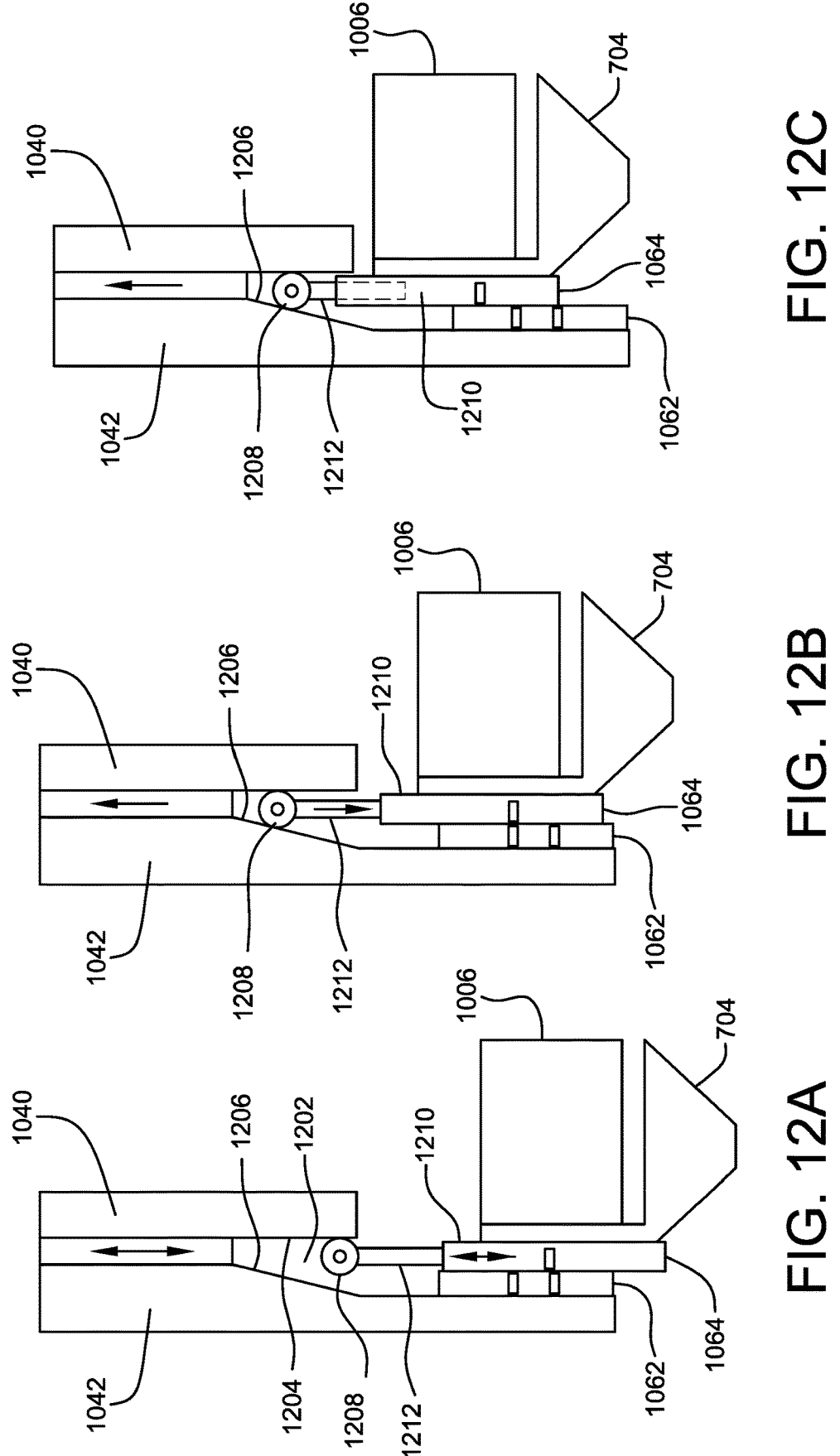
FIGS. 12A, 12B, and 12C are schematic illustrations of a mechanical one-way brake of an ophthalmic surgical system shown at different stages of a docking procedure.

With reference to FIGS. 12A, 12B, and 12C, a mechanical one-way brake 1039 may be a mechanical mechanism configured to utilize the difference of friction between surfaces when sliding or rolling. In one configuration, the mechanical mechanism of the one-way brake 1039 includes a wedge space 1202 constructed between a first surface 1204 of a coarse backplate 1040 and second surface 1206 of a coarse travel plate 1042, and a roller 1208 located in the wedge space 1202. The roller 1208 is configured to slide along the length of the wedge and is coupled to an actuator 1210 by a pushrod 1212. The actuator 1210 is configured to position the roller 1208 along the length of the wedge space 1202 to contact only the first surface 1204 (as shown in FIG. 12A) or to contact both of the first surface and the second surface 1206 (as shown in FIG. 12B). The actuator 1210 (with roller 1208) is mounted on the short-range slide mechanism 1032 and moves together with the fine travel plate 1064.

With reference to FIGS. 12A and 12B, as the fine travel plate 1064 moves up from the location shown in FIG. 12A to the location shown in FIG. 12B, the actuator 1210 pushes the roller 1208 to roll along the first surface 1204 of the coarse backplate 1040 into a narrow portion of the wedge space 1202 to a position where the roller contacts the first surface 1204 and the second surface 1206 of a coarse travel plate 1042. This action by the actuator 1210 presses the roller 1208 hard against the second surface 1206 of a coarse travel plate 1042 to prevent further upward movement of the roller. With the roller 1208 wedged between the facing surfaces 1204, 1206 of the coarse backplate 1040 and the coarse travel plate 1042, movement of the coarse travel plate toward the reference plane 1020 is prevented. Thus, one-way braking action of the long-range slide mechanism 1030 is initiated. In other words, the mechanical one-way brake is in a locked state. Setting of the starting setpoint of the one-way brake activation may be achieved by adjusting the length of the pushrod 1212 of the actuator 1210 or by adjusting the width of the wedge space 1202. In one configuration, the force level that activates the one-way brake is set to around 0.6 N.

With reference to FIG. 12C, the pushrod 1212 of the actuator 1210 may include a light force compression spring, 0.1 N or less, which allows compression of the pushrod 1212 after the one-way brake is activated. The allows for further upward movement of the surgical head 1006 in case the patient moves under the surgical head and pushes the fine travel plate 1064 further upward.

Safety Features

Returning to FIG. 11, the control system may be configured to implement various safety features. For example, the brake control module 1120 may be configured to lock the vertical brake system 1035 when both the eye attachment sensor and the cone attachment sensor provide sensor signals 1121 indicative of valid couplings to prevent lifting of the surgical head 1006.

In some embodiments, the vertical brakes 1035 are configured to enter a locked state in case of power failure. However, the holding forces of the vertical brakes 1035 are set to a level such that the surgical head 1006 can be manually lifted upward away from the patient without excessive force from the operator.

Additional safety features prevent lifting of the surgical head 1006 at the end of the procedure while the patient is still docked, the eye attachment mechanism is active, and the cone attachment mechanism is active. The features are as follows. To deactivate the eye attachment mechanism a burst of positive pressure is applied to and air flows into the suction ring of the patient interface 800. This prevents the vacuum still being present on the suction ring even though the vacuum pressure has been reduced to zero at the vacuum pump. This event can possibly happen if fluids or high viscosity gel blocks the vacuum port, or the tubes connected to the patient interface 800. Applying a short burst of positive pressure and air flow into the patient interface 800 will unblock any obstruction in the vacuum line. Sensing and confirming positive air flow or pressure confirms that the patient interface 800 is disconnected, and the brakes of the brake system can be unlocked for undocking.

Figure 13:
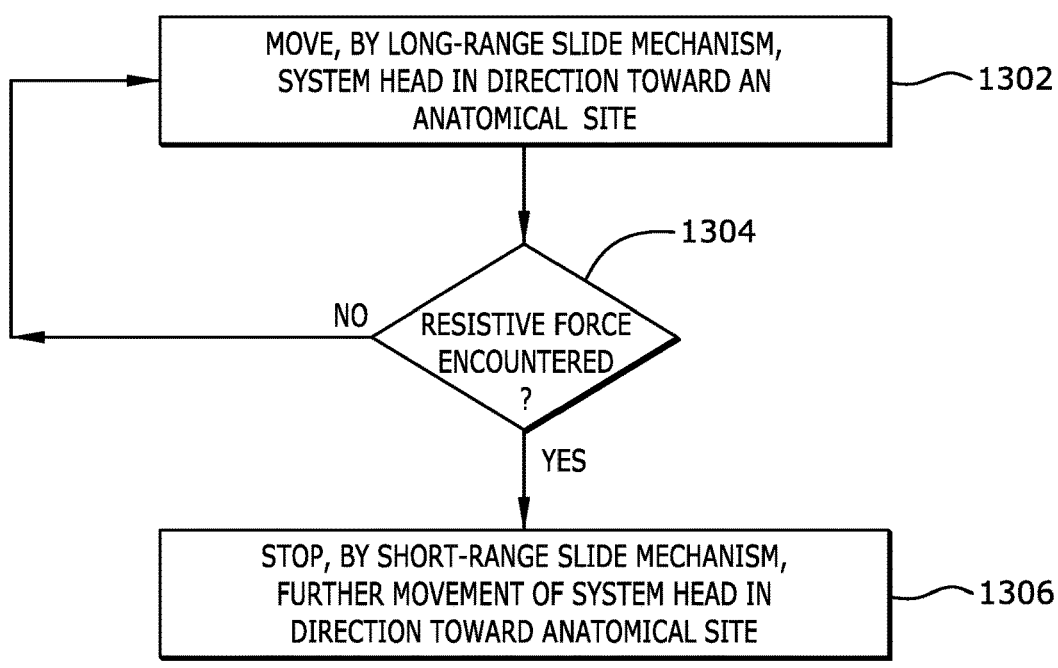
FIG. 13 is a flowchart of a method of moving a head of a medical system relative to an anatomical site.

FIG. 13 is a flowchart of a method of moving a head of a medical system relative to an anatomical site in a way that protects against unnecessary forces on the anatomical site. The method may be enabled by a medical system, such as the surgical system 1000 disclosed herein.

More specifically, with reference to FIGS. 4A and 4B, the method may be enabled by a medical system 1000 that includes a delivery arm assembly having a head 1006 with an end arranged to face a reference plane 1020 of the medical system, and a multistage slide mechanism 1008 coupled to the head. The multistage slide mechanism 1008 includes a long-range slide mechanism 1030 (or coarse-float mechanism) and a short-range slide mechanism 1032 (or fine-float mechanism). The long-range slide mechanism 1030 (to which the head 1006 is attached via the short-range slide mechanism 1032) is configured to move the head in a direction toward the reference plane 1020. The reference plane 1020 may, for example, correspond to bed upon which a patient with an anatomical site may lie during a procedure. The short-range slide mechanism 1032 is configured to stop movement of the head 1006 in the direction toward the reference plane 1020 in response to a resistive force against continued movement of the head toward the reference plane 1020.

Returning to FIG. 13 and with additional reference to FIGS. 7A and 7B, the method of moving a head 1006 of a medical system 1000 relative to an anatomical site in a way that protects against unnecessary forces on the anatomical site begins at block 1302, where the head 1006 is moved by a long-range slide mechanism 1030 in a direction toward the anatomical site, e.g., an eye 1. With reference to FIG. 7B, movement of the long-range slide mechanism 1030 in a direction toward the anatomical site may result from an application of downward force F at the handle 1012. The head 1006 is attached to the long-range slide mechanism 1030 via the short-range slide mechanism 1032 and thus moves together with the long-range slide mechanism.

At block 1304, and with additional reference to FIGS. 7C and 7D, in response to a resistive force (or counter force) against movement of the head 1006 in the direction toward the anatomical site 1, the method proceeds to block 1306, where further movement of the head 1006 in the direction toward the anatomical site is stopped by the short-range slide mechanism 1032. The resistive force R (or counter force) against movement of the head 1006 in the direction toward the anatomical site 1 occurs as the head 1006 is moved further downward from its location shown in FIG. 7B to its location shown in FIG. 7C. At the location of the head 1006 shown in FIG. 7C, an initial contact between the cone attachment 704 of the head and the interior of the patient interface 800 results in the resistive force R. Stoppage of further movement of the head 1006 by the short-range slide mechanism 1032 in the direction toward the anatomical site does not impede movement of the long-range slide mechanism 1030. This is evident in comparing FIG. 7C and FIG. 7D, where the coarse travel plate 1042 of the long-range slide mechanism 1030 and the fine backplate 1062 of the short-range slide mechanism 1032 continue to move toward the anatomical site 1.

Returning to block 1304, if a resistive force R against movement of the head 1006 in the direction toward the anatomical site 1 is not present, the method returns to block 1302 and the head 1006 is moved further by the long-range slide mechanism 1030 in the direction toward the anatomical site 1.

Figure 14:
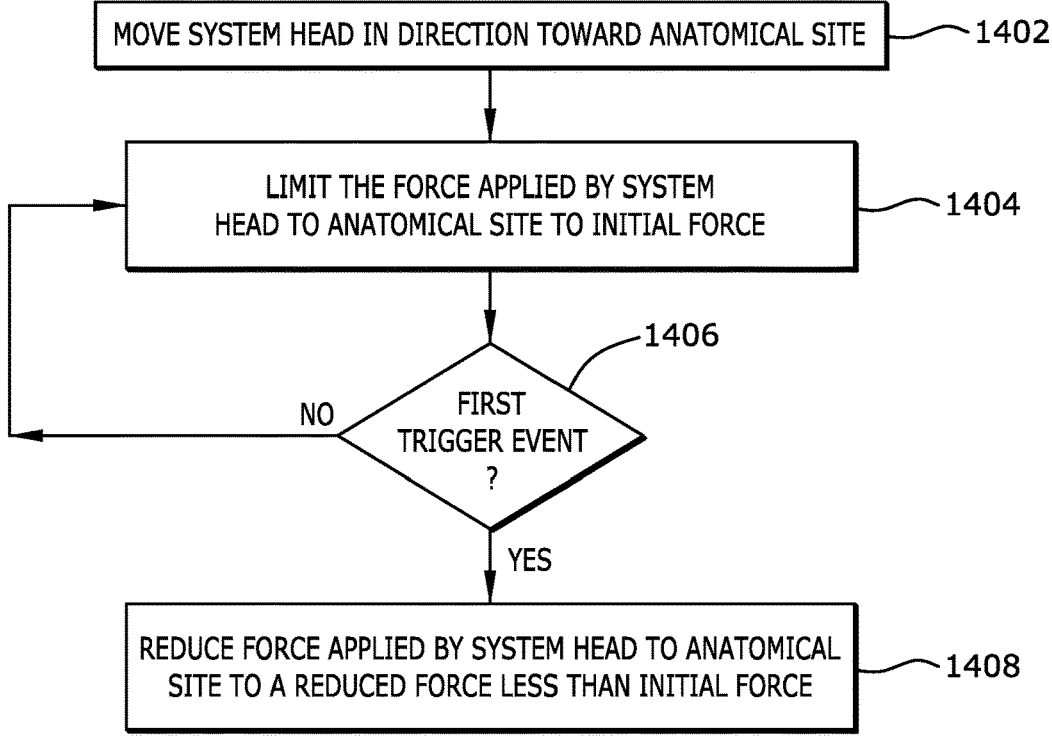
FIG. 14 is a flowchart of a method of coupling a head of a medical system relative to an anatomical site.

FIG. 14 is a flowchart of a method of coupling a head of a medical system with respect to an anatomical site in a way that protects against prolonged application of an initial force to the anatomical site. The method may be enabled by a medical system, such as the surgical system 1000 disclosed herein.

More specifically, with reference to FIGS. 4A and 4B, the method may be enabled by a medical system 1000 that includes a head 1006 having an end arranged to face a reference plane 1020, and a multistage slide mechanism 1008 coupled with the head. The multistage slide mechanism 1008 includes a coarse-float mechanism 1030 and a fine-float mechanism. The coarse-float mechanism 1030 is configured to enable movement of the head 1006 relative to the reference plane 1020. The reference plane 1020 may, for example, correspond to bed upon which a patient with an anatomical site may lie during a surgical procedure. The fine-float mechanism 1032 is configured to limit a force applied through the head 1006 to an initial force, and to reduce the force applied through the head to a reduced force less than the initial force in response to a presence of a first triggering event.

Returning to FIG. 14 and with additional reference to FIGS. 7B and 7C, the method of coupling a head 1006 of a medical system 1000 to an anatomical site in a way that protects against prolonged application of an initial force to the anatomical site begins at block 1402, where a head 1006 is moved relative to the anatomical site, e.g., an eye 1.

At block 1404, and with additional reference to FIG. 7C, a force applied by the head 1006 to the anatomical site is limited to an initial force $H_I$. As disclosed above with reference to FIGS. 8A and 8B, this initial force $H_I$ may be set by a counterbalance mechanism 1066 of the short-range slide mechanism 1032 that places the short-range slide mechanism in a heavy mode.

At block 1406, and with additional reference to FIG. 7D, in response to a presence of a first triggering event, the method proceeds to block 1408 where the force applied by the head 1006 to the anatomical site 1 is automatically reduced to a reduced force $H_R$ less than the initial force $H_I$. The first triggering event may be a presence of a valid coupling between the cone attachment 704 of the head 1006 and the patient interface 800. The reduced force $H_R$ may be set by adjusting the counterbalance mechanism 1066 of the short-range slide mechanism 1032 to enter a light mode.

Returning to block 1406, in the absence of the first triggering event, the method returns to block 1404 where the force applied by the head 1006 to the anatomical site 1 remains limited to the initial force.

Figure 15:
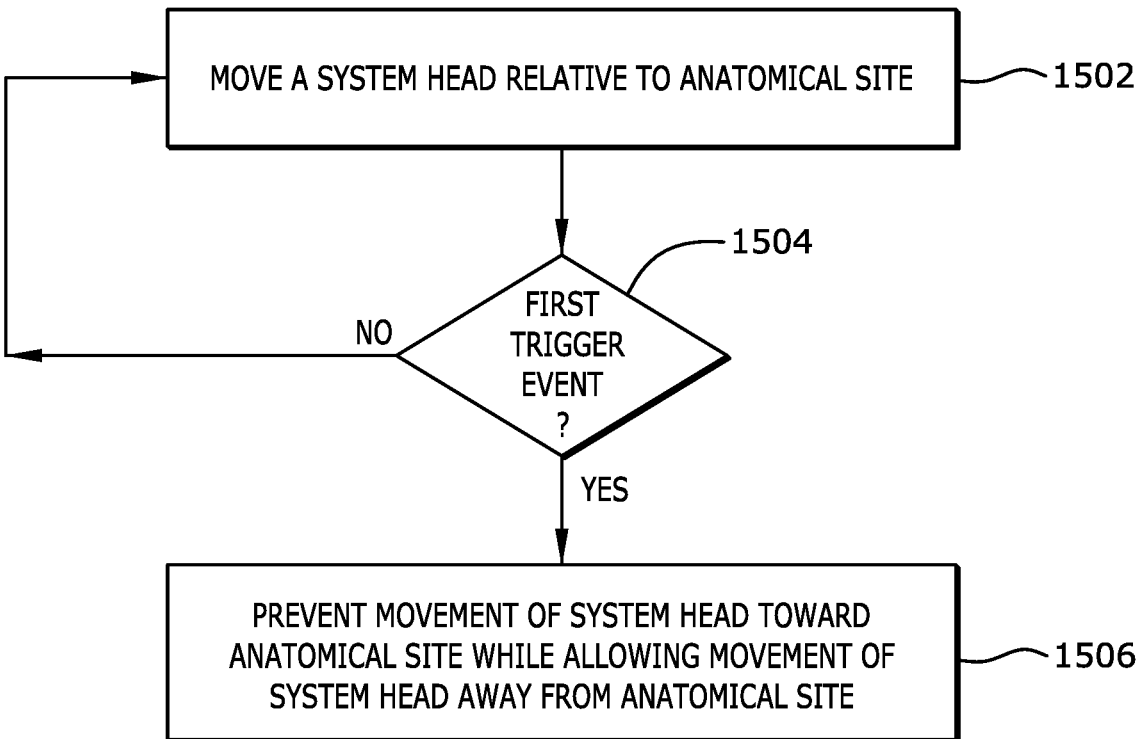
FIG. 15 is a flowchart of a method of coupling a head of a medical system relative to an anatomical site.

FIG. 15 is a flowchart of a method of coupling a head of a medical system to an anatomical site in a way that further protects against unnecessary forces on the anatomical site. The method may be enabled by a medical system, such as the surgical system 1000 disclosed herein.

More specifically, with reference to FIGS. 4A and 4B, the method may be enabled by a medical system 1000 that includes a head 1006 having an end arranged to face a reference plane 1020, and a multistage slide mechanism 1008 coupled with the head. The multistage slide mechanism 1008 includes a coarse-float mechanism 1030 configured to enable movement of the head 1006 relative to the reference plane 1020. The reference plane 1020 may, for example, correspond to surgical bed upon which a patient with an anatomical site may lie during a surgical procedure. The coarse-float mechanism 1030 is further configured to prevent movement of the head 1006 toward the reference plane 1020 while allowing movement of the head away from the reference plane, in response to a presence of a first triggering event.

Returning to FIG. 15 and with additional reference to FIGS. 7B and 7C, the method of coupling a head 1006 of a medical system 1000 to an anatomical site in a way that further protects against unnecessary forces on the anatomical site begins at block 1502, where the head 1006 is moved relative to the anatomical site, e.g., an eye 1.

At block 1504, and with additional reference to FIGS. 7C, 7D, and 7E, in response to a presence of a first triggering event, the method proceeds to block 1506, where movement of the head 1006 toward the anatomical site 1 is prevented while movement of the head away from the anatomical site is allowed. To this end, a one-way brake 1039 of the coarse-float mechanism 1030 is activated. The one-way brake 1039 is configured to simultaneously prevent movement of the head 1006 toward the anatomical site 1 and allow movement of the head away from the anatomical site. The first triggering event may be a presence of a valid coupling between the cone attachment 704 of the head 1006 and the patient interface 800 that results from movement of the head toward the anatomical site 1 and into contact with a patient interface 800, and locking of the head with the patient interface, as illustrated sequentially in FIGS. 7C, 7D, and 7E.

Returning to block 1504, in the absence of the first triggering event, the method returns to block 1502, where the head 1006 is moved further relative to the anatomical site 1.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A delivery arm assembly of a medical system, the delivery arm assembly comprising:
   a head having an end arranged to face a reference plane; and
   a multistage slide mechanism coupled to the head and configured to move the head along an axis relative to the reference plane and in a direction toward the reference plane, the multistage slide mechanism comprising:
      a long-range slide mechanism; and
      a short-range slide mechanism arranged between the head and the long-range slide mechanism, the short-range slide mechanism comprising a fine backplate fixedly coupled to the long-range slide mechanism and a fine travel plate slidably coupled to the fine backplate and fixedly coupled to the head, the fine travel plate configured to move together with the fine backplate and the long-range slide mechanism along the axis toward the reference plane until a resistive force against movement of the head toward the reference plane is encountered by the fine travel plate, at which time the fine travel plate stops moving while the fine backplate and the long-range slide mechanism continue to move along the axis.

2. The delivery arm assembly of claim 1, wherein the short-range slide mechanism is configured to limit movement of the fine travel plate relative to the long-range slide mechanism to a short-range distance.

3. The delivery arm assembly of claim 1, wherein the long-range slide mechanism comprises a long-range counterbalance mechanism configured to apply a counterbalance force against a force of a load mass comprising the head.

4. The delivery arm assembly of claim 1, wherein the long-range slide mechanism is configured to limit movement of the head in a direction toward the reference plane to a long-range distance.

5. The delivery arm assembly of claim 1, wherein the resistive force against movement of the head toward the reference plane is in a range of −0.5N and +0.5N.

6. A delivery arm assembly of a medical system, the delivery arm assembly comprising:
   a head having an end arranged to face a reference plane;
   a multistage slide mechanism coupled to the head and comprising:
      a long-range slide mechanism configured to move the head in a direction toward the reference plane; and
      a short-range slide mechanism coupled with the long-range slide mechanism and configured to, in response to a resistive force against movement of the head toward the reference plane, stop further movement of the head in the direction toward the reference plane; and
   a sensor configured to detect a triggering event, wherein the long-range slide mechanism is configured to prevent movement of the head in a direction toward the reference plane in response to a detection of a trigger event.

7. The delivery arm assembly of claim 6, wherein the sensor comprises a displacement sensor and the triggering event corresponds to a threshold displacement of a fine travel plate of the short-range slide mechanism.

8. The delivery arm assembly of claim 6, wherein the sensor comprises a force sensor and the triggering event corresponds to a threshold force against movement of a fine travel plate of the short-range slide mechanism in a direction toward the reference plane.

9. A medical system comprising:
   a delivery arm assembly including:
      a head having an end arranged to face a reference plane;
      a delivery arm configured to enable lateral movement of the head relative to the reference plane; and
      a multistage slide mechanism coupled to the head and configured to move the head along an axis relative to the reference plane and in a direction toward the reference plane, the multistage slide mechanism comprising a long-range slide mechanism, and a short-range slide mechanism with arranged between the head and the long-range slide mechanism, the short-range slide mechanism comprising a fine backplate fixedly coupled to the long-range slide mechanism and a fine travel plate slidably coupled to the fine backplate and fixedly coupled to the head, the fine travel plate configured to move together with the fine backplate and the long-range slide mechanism along the axis toward the reference plane until a resistive force against movement of the head toward the reference plane is encountered by the fine travel plate, at which time the fine travel plate stops moving while the fine backplate and the long-range slide mechanism continue to move along the axis; and
   a brake system configured to transition between a locked state and an unlocked state, wherein:
      in the locked state, lateral movement of the head through the delivery arm is prevented and movement of the head through the long-range slide mechanism is prevented, and
      in the unlocked state, lateral movement of the head through the delivery arm is enabled and movement of the head through the long-range slide mechanism is enabled.

10. The medical system of claim 9, wherein the long-range slide mechanism comprises:

a coarse backplate;

a coarse travel plate slidably coupled to the coarse back-plate; and a long-range counterbalance mechanism configured to apply a counterbalance force against a force of a load mass comprising the head.

11. A medical system comprising:

a delivery arm assembly including:

a head having an end arranged to face a reference plane;

a delivery arm configured to enable lateral movement of the head relative to the reference plane; and a multistage slide mechanism comprising a long-range slide mechanism configured to enable movement of the head in a direction toward the reference plane, and a short-range slide mechanism coupled with the long-range slide mechanism and configured to, in response to a resistive force against movement of the head toward the reference plane, stop further movement of the head in the direction toward the reference plane, the short-range slide mechanism comprising a fine backplate coupled to the long-range slide mechanism; a fine travel plate slidably coupled to the fine backplate; and a short-range counterbalance mechanism configured to define the resistive force that stops further movement of the head in the direction toward the reference plane, wherein the short-range counterbalance mechanism comprises at least one magnetic coupling including structures arranged to provide an air gap that defines the resistive force; and a brake system configured to transition between a locked state and an unlocked state, wherein:

in the locked state, lateral movement of the head through the delivery arm is prevented and movement of the head through the long-range slide mechanism is prevented, and in the unlocked state, lateral movement of the head through the delivery arm is enabled and movement of the head through the long-range slide mechanism is enabled.

12. The medical system of claim 11, wherein the structures comprise one of:

a pair of magnets spaced apart to define the air gap; and a metal plate and a magnet spaced apart to define the air gap.

13. The medical system of claim 2, wherein the structures comprise:

an intermediate fine-travel magnet that is mechanically coupled to the fine travel plate; and a pair of metal plates that are mechanically coupled to the long-range slide mechanism through the fine backplate, wherein the intermediate fine-travel magnet is positioned between the pair of metal plates so that the air gap is present between a first surface of the intermediate fine-travel magnet and at least one of the metal plates.

14. The medical system of claim 13, wherein the pair of metal plates comprises:

a magnetic pivot plate configured and arranged to be repositioned relative to the first surface of the intermediate fine-travel magnet to thereby change a size of the air gap; and a fixed plate positioned relative to a second surface of the intermediate fine-travel magnet.

15. The medical system of claim 11, further comprising one or more mechanical actuation buttons configured to output control signals to the brake system to transition the brake system between a locked state and an unlocked state.

16. The medical system of claim 11, further comprising one or more sensors configured to output control signals to the brake system to transition the brake system between a locked state and an unlocked state.

17. The medical system of claim 11, wherein the long-range slide mechanism comprises:

a coarse backplate;

a coarse travel plate slidably coupled to the coarse back-plate; and a long-range counterbalance mechanism configured to apply a counterbalance force against a force of a load mass comprising the head.

18. A medical system comprising:

a delivery arm assembly including:

a head having an end arranged to face a reference plane;

a delivery arm configured to enable lateral movement of the head relative to the reference plane;

a multistage slide mechanism comprising a long-range slide mechanism configured to enable movement of the head in a direction toward the reference plane, and a short-range slide mechanism coupled with the long-range slide mechanism and configured to, in response to a resistive force against movement of the head toward the reference plane, stop further movement of the head in the direction toward the reference plane;

a brake system configured to transition between a locked state and an unlocked state, wherein:

in the locked state, lateral movement of the head through the delivery arm is prevented and movement of the head through the long-range slide mechanism is prevented, and in the unlocked state, lateral movement of the head through the delivery arm is enabled and movement of the head through the long-range slide mechanism is enabled; and a sensor configured to:

detect a triggering event resulting from movement of the head toward the reference plane; and output one or more control signal to the brake system to transition the brake system to a locked state that prevents movement of the head in a direction toward the reference plane.

19. The medical system of claim 18, wherein the sensor comprises a displacement sensor and the triggering event corresponds to a threshold displacement of a fine travel plate of the short-range slide mechanism.

20. The medical system of claim 18, wherein the sensor comprises a force sensor and the triggering event corresponds to a threshold force against movement of a fine travel plate of the short-range slide mechanism in a direction toward the reference plane.

* * * * *